US008247173B2

(12) United States Patent
Ranum et al.

(10) Patent No.: US 8,247,173 B2
(45) Date of Patent: *Aug. 21, 2012

(54) SPINOCEREBELLAR ATAXIA TYPE 8 AND METHODS OF DETECTION

(75) Inventors: Laura P. W. Ranum, St. Paul, MN (US);
Michael D. Koob, Roseville, MN (US);
Kellie A. Benzow, Plymouth, MN (US);
Melinda L. Moseley-Alldredge, St. Paul, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/819,749

(22) Filed: Jun. 21, 2010

(65) Prior Publication Data

US 2010/0317015 A1 Dec. 16, 2010

Related U.S. Application Data

(63) Continuation of application No. 10/373,667, filed on Feb. 24, 2003, now Pat. No. 7,741,458, which is a continuation of application No. 09/181,585, filed on Oct. 28, 1998, now Pat. No. 6,524,791.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ........ 435/6.1; 435/91.2; 536/23.1; 536/24.3

(58) Field of Classification Search .................. None
See application file for complete search history.

(56) References Cited

U.S. PATENT DOCUMENTS

| | | | |
|---|---|---|---|
| 4,683,194 | A | 7/1987 | Saiki et al. |
| 4,683,195 | A | 7/1987 | Mullis et al. |
| 5,558,988 | A | 9/1996 | Prockop et al. |
| 5,695,933 | A | 12/1997 | Schalling et al. |
| 5,741,645 | A | 4/1998 | Orr et al. |
| 5,807,743 | A | 9/1998 | Stinchcomb |
| 5,834,183 | A | 11/1998 | Orr et al. |
| 6,183,953 | B1 | 2/2001 | Raymond |
| 6,524,791 | B1 | 2/2003 | Ranum et al. |
| 7,741,458 | B2 | 6/2010 | Ranum et al. |

FOREIGN PATENT DOCUMENTS

| | | |
|---|---|---|
| WO | 95/01437 | 1/1995 |
| WO | 97/42314 | 11/1997 |

OTHER PUBLICATIONS

Accession No. AL008632, Apr. 3, 1998.
Alignment for AR039405 (result 77) Sep. 2011.
Alignment for AR128104 (result 15) Sep. 2011.
Alignment for Genbank Accession No. E09524, Sep. 1997.
Alignment for I26375 (result 70) Sep. 2011.
Alignment for Schalling 5,695,933 (result 17) Sep. 2011.
Alignment for WO9501437 (result 6) Sep. 2011.
Alignment-Blast: for AF126748.1 and gi: 7249018 Sep. 2011.
Ashizawa et al., "Anticipation in myotonic dystrophy. II. Complex relationships between clinical findings and structure of the GCT repeat," *Neurology*, 1992; 42: 1877-1883.
Benomar et al., "The gene for autosomal dominant cerebellar ataxia with pigmentary macular dystrophy maps to chromosome 3p12-p21.1," *Nature Genet.*, 1995; 10: 84-8.
David et al., "Cloning of the SCA7 gene reveals a highly unstable CAG repeat expansion," *Nature Genet.*, 7 65-70 (1997).
e-mail of Pieter J. de Jong, Ph.D.
Gardner et al., "Autosomal Dominant Spinocerebellar Ataxia: Clinical Description of a Distinct Hereditary Ataxia and Genetic Localization to Chromosome 16 (SCA4) in a Utah Kindred," Abstract 921S, *Neurology*, 1994; 44: A361.
Gispert et al., "Chromosomal assignment of the second locus for autosomal dominant cerebellar ataxia (SCA2) to chromosome 12q23-24.1," *Nature Genet.*, 1993; 4: 295-299.
Gouw et al., "Retinal degeneration characterizes a spinocerebellar ataxia mapping to chromosome 3p," *Nature Genet.*, 1995; 10: 89-93.
Hernandez et al., "ENC-1: A Novel Mammalian Kelch-Related Gene Specifically Expressed in the Nervous System Encodes an Actin-Binding Protein," *J Neurosci*, 1997; 17: 3038-51.
Ikeda et al; "Bidirectional expression of the SCA8 expansion mutation: one mutation, two genes," *The Cerebellum*, 2008; 1-9.
Imbert et al., "Cloning of the gene for spinocerebellar ataxia 2 reveals a locus with high sensitivity to expanded CAG/glutamine repeats," *Nature Genet.*, 1996; 14: 285-291.
Kawaguchi et al., "CAG expansions in a novel gene for Machado-Joseph disease at chromosome 14q32.1," *Nature Genet.*, 1994; 8: 221-228.
Kim et al., "NRP/B, a Novel Nuclear Matrix Protein, Associates With p110$^{RB}$ and Is Involved in Neuronal Differentiation,"*J. Cell Biol.*, 1998; 141: 553-66.
Koide et al., "Unstable expansion of CAG repeat in hereditary dentatorubralpallidoluysian atrophy (DRPLA)," *Nature Genet.*, 1994; 6: 9-13.
Koob et al., "A 3' untranslated CTG repeat causes spinocerebellar ataxia type 8 (SCA8)," abstract, www.faseb.org/genetics/ashg/annmeet, published Sep. 30, 1998.
Koob et al., "Rapid cloning of expanded trinucleotide repeat sequences from genomic DNA," *Nature Genet.*, 1998; 18: 72-5.
Lathrop et al., "Strategies for multilocus linkage analysis in humans," *Proc. Natl. Acad. Sci. USA*, 1984; 81: 3443-6.
Levitan, Textbook of Human Genetics, 3ed. Oxford University Press, NY 1988.
Lindblad et al., "An expanded CAG Repeat Sequence in Spincerebellar Ataxia Type 7," *Genome Research*, 1996; 6:965-71.
Lindblad et al., *American Journal of Human Genetics*, Oct.-Nov. 1996; 59(4 Suppl.): A269, Meeting Abstract.
Maxam et al., "Sequencing End-Labeled DNA with Base-Specific Chemical Cleavages," *Methods in Enzymology*, 1980; 65: 499-557.
Messing et al., "A system for shotgun DNA sequencing," *Nucl. Acids Res.*, 1981; 9: 309-21.

(Continued)

*Primary Examiner* — Jehanne Sitton
(74) *Attorney, Agent, or Firm* — Mueting Raasch & Gebhardt, P.A.

(57) ABSTRACT

The present invention provides an isolated nucleic acid molecule containing a repeat region of an isolated spinocerebellar ataxia type 8 (SCA8) coding sequence, the coding sequence located within the long arm of chromosome 13, and the complement of the nucleic acid molecule. Diagnostic methods based on identification of this repeat region are also provided.

17 Claims, 10 Drawing Sheets

OTHER PUBLICATIONS

Moseley et al; "Bidirectional expression of CUG and CAG expansion transcripts and intranuclear polyglutamine inclusions in spinocerebellar ataxia type 8," *Nature Genetics*, Jul. 2006; 38(7): 758-69.

Moseley et al., "Frequency and dramatic instability of the 3' untranslated CTG repeat causing spinocerebellar ataxia type 8 (SCA8)," abstract, www.faseb.org/genetics/ashg/ann-meet, published Sep. 30, 1998.

Nagafuchi et al., "Dentatorubral and pallidoluysian atrophy expansion of an unstable CAG trinucleotide on chromosome 12p," *Nature Genet.*, 1994; 6: 14-8.

National Center for Biotechnology Information, National Library of Medicine, National Institutes of Health, GenBank Locus MMU80889, Accession No. U80889, " Mus musculus CAG trinucleotide repeat mRNA, partial sequence," [online]. Bethesda, MD [retrieved on Sep. 23, 2011]. Retrieved from the Internet:<URL: http://www.ncbi.nlm.nih.gov/nuccore/67045127>.

National Center for Biotechnology Information, National Library of Medicine, National Institutes of Health, GenBank Locus 2355723, Accession No. AA580396, "nn13g04.s1 NCI_CGAP_Co12 Homo sapiens cDNA clone IMAGE:1083798 3—similar to contains MER14.b3 MER14 repetitive element ;, mRNA sequence," [online]. Bethesda, MD [retrieved on Sep. 23, 2011]. Retrieved from the Internet<URL:http://www.ncbi.nlm.nih.gov/nucest/2355723>.

National Center for Biotechnology Information, National Library of Medicine, National Institutes of Health, GenBank Locus 1477254, Accession No. AA016151, " ze17c05.s1 Soares_fetal_heart_ NbHH19W Homo sapiens cDNA clone IMAGE:359240 3-, mRNA sequence," [online]. Bethesda, MD [retrieved on Sep. 23, 2011]. Retrieved from the Internet<URL: http://www.ncbi.nlm.nih.gov/nucest/aa016151>.

National Center for Biotechnology Information, National Library of Medicine, National Institutes of Health, GenBank Locus AC013803, Accession No. AC013803, "Homo sapiens clone RP11-20M9, Working Draft Sequence, 12 unordered pieces," [online]. Bethesda, MD [retrieved on May 12, 2011]. Retrieved from the Internet:<URL: http://www.ncbi.nlm.nih.gov/nuccore/AC013803>.

Nemes et al., "The SCA8 transcript is an antisense RNA to a brain-specific transcript encoding a novel actin-binding protein (KLHL1)" *Human Molecular Genetics*, Apr. 2000; 9(10): 1543-51.

Nikali et al., "Toward Cloning of a Novel Ataxia Gene: Refined Assignment and Physical Map of the IOSCAS Locus (SCA8) on 10q24," *Genomics*, Jan. 15, 1997; 39(2): 185-191.

Orr et al., "Expansion of an unstable trinucleotide CAG repeat in spinocerebellar ataxia type 1," *Nature Genet.*, 1993; 4: 211-26.

Ott, *Analysis of Human Genetic Linkage, Revised Edition*, The Johns Hopkins University Press, Baltimore, MD, title page and table of contents (1991).

Pulst et al., "Moderate expansion of a normally biallelic trinucleotide repeat in spinocerebellar ataxia type 2," *Nature Genet.*, 1996; 14: 269-76.

Ranum et al., "Spinocerebellar Ataxia Type 1 and Machado-Joseph Disease: Incidence of CAG Expansions among Adult-Onset Ataxia Patients from 311 Families with Dominant, Recessive, or Sporadic Ataxia," *Am. J. Hum. Genet.*, 1995; 57: 603-8.

Ranum et al., "Spinocerebellar ataxia type 5 in a family descended from the grandparents of President Lincoln maps to chromosome 11," *Nature Genet.*, 1994; 8: 280-4.

Ranum, Laura "Molecular Genetic Characterization of SCA8," Grant Abstract, Grant No. P01 NS 33718 [online], NIH, Jun. 16, 2000 to Mar. 31, 2012 [retrieved on May 12, 2012]. Retrieved from the Internet: <URL: http://projectreporter.nih.gov>.

Robinson et al., "Drosophila Kelch Is an Oligomeric Ring Canal Actin Organizer," *J. Cell Biol.*, 1997; 138: 799-810.

Saiki et al., "Enzymatic amplication of beta-globin genomic sequences and restriction site analysis for diagnosis of sickle cell anemia" *Science*, 1985; 230(4732): 1350-4.

Sambrook et al., *Molecular Cloning: A Laboratory Manual*, Cold Spring Harbor Laboratory: New York, 11.2-11.4 (1993).

Sambrook et al., *Molecular Cloning: A Laboratory Manual*, Cold Spring Harbor Laboratory: New York, cover page and table of contents (1989).

Sanpei et al., "Identification of the spinocerebellar ataxia type 2 gene using a direct identification of repeat expansion and cloning technique, DIRECT," *Nature Genet.*, 1996; 14: 277-84.

Scharf et al., "Direct Cloning and Sequence Analysis of Enzymatically Amplified Genomic Sequences," *Science*, 1986; 233: 1076-8.

Takiyama et al., "The gene for Machado-Joseph disease maps to human chromosome 14q," *Nature Genet.*, 1993; 4: 300-4.

Tanaka et al., "Age of onset-specific central nervous system disorders Spinocerebellar degeneration and prediliection age," *Clin. Neurosci.*, 1998; 16(1): 43-6, and English Translation.

Vincent et al., "Unstable DNA in major psychoses: cloning of a new unstable trinucleotide repeat region on chromosome 13," abstract, www.faseb.org/genetics/ashg/ann-meet, published Sep. 30, 1998.

Yabe et al., "Hereditary spinocerebellar degeneration," *J Sen Dement*, 1998; 12(3): 299-311. and English Translation.

Zhuchenko et al., "Autosomal dominant cerebellar ataxia (SCA6) associated with small polyglutamine expansions in the $\alpha_{1A}$-voltage-dependent calcium channel," *Nature Genet.*, 1997; 15: 62-9.

Fig. 7a

GAATTCATGCCTATAATTTATAAGATCTGCCACCCTACCAGCCTTACTGTTTTTCTCATT
GGTAATATTCATGAAGTCACTGGTAATTTTACATTTTAAAATATGCAGTATGAATTGCAT
ATATAGTACTTCTTAAATGTCAACACATTTATCTTAAATCATTTATCGAAGTATGAGAAG
TACCTATCATATTTTGGTAAATAATACCTTTAGGTTTTTCCTAGTTCTTGGCTCCAGACT
AACCATCTTGACCTGTCATTCTAGTTTTTACTTCTGAGACATTCTATAGTCTGTGTCTGA
TATTCTCTACTATTTCCTCATTTGTCCTTGCATTCAGATTGCCTTTTCTGACTCCCAGCT
TCCACGGAGAGATTAACTCTGTTGGCTGAAGCCCTATCCCAATTCCTTGGCTAGACCCTG
GGTCCTTCATGTTAGAAAACCTGGCTTTACTACTACTACTACTACTACTACTACTACTAC
TACTGCTACTGCTGCTGCTGCTGCTGCTGCTGCTGCTGCTGCTGCTGCTGCTGCTGCTGC
TGCTGCTGCTGCTGCTGCTGCTGCTGCTGCTGCTGCTGCTGCTGCTGCTGCTGCTGCTGC
TGCTGCTGCTGCTGCTGCTGCTGCTGCTGCTGCTGCTGCTGCTGCTGCTGCTGCTGCTGC
TGCTGCTGCTGCTGCTGCTGCTGCTGCTGCTGCTGCTGCTGCTGCTGCTGCTGCTGCTGC
TGCTGCATTTTTAAAAATATATTATCTTATTTTACTATTTGATGTTATAATTGTTATAT
ATTTTTCCATACTTCCTCATACTGCTTATCTCTTACTTAAGAATTTATGAATAAAGAATT
GATTTTTCAATACATCCTTCCAAAAATTATCTGATGTTGAGTTAGTTGCTCTCTCTTGTG
CATTCTCAGTCCTCACAAGCCTTTCTCAAACACAATGTTTATCAAAGAAAATTGTAGCAA
CCAATATACTTAGTGGAATTTCTCACAGAGTTTGAGTGTAGGAAACAGTATTCACTGTAT
ATTAGTCATTTTGCTCCCAATAGAAGGTGCATAACATAAATTATTTAAGTGGATGAATGC
TTTATTTTCCTTTATAAAAGTACCTTCTTGCTTCACTGACATTTCTATACAACTATTCTT
GTAAGCAAGGAATGAATTC

Fig. 7b

ATCCTTCACCTGTTGCCTGGCTAGAGTTGTCTGGCTCCACTTTGAGCTCTTGCAGAACCA
GCCCTTTTTCGTGTGGTCCAGGAAAGTCCATGCCTGGCACCACCTCCTCCTCTAGTGACT
CCACGTAGAAGAGAGTCCTGGCTGGCTGCTGAGTGCCCTGCCCAGGAGCCCCTTGCTGCA
GCCTCGTGGCAACTGGAAGCAGGGTGCCATTCAGCGGATTGAAGGAAGAGGAGGAAGAGG
ACGGGGAGGACGATGAAGAGGAAGAGGAGGAAGGCTTCTTCCAGAAAGTGCTCACACCGC
TTCTCTCTTGGCTTTTGAGCAGGCGACTCTGGCTGGGTCCCAGTGCTCAAAGCTGCCAC
TGCCGTCCTGTTGCAGGCAGCCTCCCCCGCCGGGCCGCCGGTGGAAGGAGACGGGTGGC
TGAAGAGTTTCCAGCGGAGTCGCAGAATGTGCTTCACATCGAAGTCTTTTCGCCCAGAGC
CTGACATGCTTTACGCACAGAAGGCAAAAGGCTGGCAGCTCACGCAGGGTTCTGGAGGCT
GGGAAGTTCAAGACCAATGCACGAGAATTTGGTCTAAAGAGAATCTTCTTGCTCTGAACA
CACATAGTAGAAGGCAGAAGGGCAAGAGAGAGAACAAAGTCTGTGTCTCCACATGGCAGA
AGAGCAGAGGAGACAGAACCTACTCCTCTATGGCAACCACCCCATCAATGACAAAAATCC
TAGAAGGATGTATGTATAGGAAGTTGAAGTGTTGAGAAGAGAATGGCTCAGAGTCAAGCG
GGAACAAGATTCAAACTTCAGAGAGAGAGGGAAGAAAAACATTTAAATATATCTGGCATA
ATCCXAGACTATTTACGACAAGTGTTCTGTGTTTCTAATAATAAAACAGACTTCACCTCG
GAGTACCTGCAGAACTGGGACCCCAATGACCAGGGAGAATGAAGAACAACTTGTTTGAAG
ATTGCCTTTTCTGACTCCCAGCTTCCACGGAGAGATTAACTCTGTTGGCTGAAGCCCTAT
CCCAATTCCTTGGCTAGACCCTGGGTCCTTCATGTTAGAAAACCTGGCTTTACTACTACT
ACTACTACTACTACTACTACTACTGCTACTGCTGCTGCTGCTGCTGCTGCTGCTGCTGCT
GCTGCTGCTGCTGCTGCTGCTGCTGCTGCTGCTGCTGCTGCTGCTGCTGCTGCTGCTGCT
GCTGCTGCTGCTGCTGCTGCTGCTGCTGCTGCTGCTGCTGCTGCTGCTGCTGCTGCTGCT
GCTGCTGCTGCTGCTGCTGCTGCTGCATTTTTTAAAAATATATTATCTTATTTTACT
ATTTGATGTTATAATTGTTATATATTTTTCCATACTTCCTCATACTGCTTATCTCTTACT
TAAGAATTTATGAATAAAGAATTGATTTTTCA

Fig. 7c

AAGCGTACCCCTCGCCAGATCTCTTGGTGCACCTGCGCCCCTGTCCCTGGCCTTTTCGAG
GATGCCCCGATAGCCTGCCGGGTGGCTCTGAGAAAGTCAATTGCTTTCTGCAATGCCAGA
AGAGGTGGTTTTATATAGTCAGTTTGTAAAAGAGAAAAATAGATATTCTAGCGCATATAG
GGAGGCAAAAGAAAAAGCCCGCCTGTGAAGCTGTCAAGGTCCTCACAGTACAATTTTCTC
TCTGCCTCAGCGCCTCCTCCTCCCCTTTCTGGAGGCTGGGAAGTTCAAGACCAATGCACG
AGAATTTGGTCTAAAGAGAATCTTCTTGCTCTGAACACACATAGTAGAAGGCAGAAGGGC
AAGAGAGAGAACAAAGTCTGTGTCTCCACATGGCAGAAGAGCAGAGGAGACAGAACCTAC
TCCTCTATGGCAACCACCCCATCAATGACAAAAATCCTAGAAGGATGTATGTATAGGAAG
TTGAAGTGTTGAGAAGAGAATGGCTCAGAGTCAAGCGGGAACAAGATTGCCTTTTCTGAC
TCCCAGCTTCCACGGAGAGATTAACTCTGTTGGCTGAAGCCCTATCCCAATTCCTTGGCT
AGACCCTGGGTCCTTCATGTTAGAAAACCTGGCTTTACTACTACTACTACTACTACTACT
ACTACTACTACTGCTACTGCTGCTGCTGCTGCTGCTGCTGCTGCTGCTGCTGCTGCTGCT
GCTGCTGCTGCTGCTGCTGCTGCTGCTGCTGCTGCTGCTGCTGCTGCTGCTGCTGCTGCT
GCTGCTGCTGCTGCTGCTGCTGCTGCTGCTGCTGCTGCTGCTGCTGCTGCTGCTGCTGCT
GCTGCTGCTGCTGCTGCTGCTGCTGCTGCTGCTGCTGCTGCTGCTGCTGCTGCTGCTGCT
GCTGCTGCTGCTGCATTTTTTAAAAATATATTATCTTATTTTACTATTTGATGTTATAAT
TGTTATATATTTTTCCATACTTCCTCATACTGCTTATCTCTTACTTAAGAATTTATGAAT
AAAGAATTGATTTTTCA

Fig. 7d

```
        AGTGG ACACAGATGG CTTCCTTGAA TATTGGGAGA GCAGGTGCCT
        TCACC TGTGTCTACC GAAGGAACTT ATAACCCTCT CGTCCACGGA

GTGTGGTAGT CATCAAGCAA CCTTGACTTA TTGATATTTT ACTTGGAAAG
CACACCATCA GTAGTTCGTT GGAACTGAAT AACTATAAAA TGAACCTTTC

ATTTTACTTG CTGGAGTGGT TATTTTTATA TTGAATGGCA AGAATGAGAA
TAAAATGAAC GACCTCACCA ATAAAAATAT AACTTACCGT TCTTACTCTT

CTTCCAGAGA TGAAAACTCT TCAAGAACAA GGATCTCTGT AGCGTTACCT
GAAGGTCTCT ACTTTTGAGA AGTTCTTGTT CCTAGAGACA TCGCAATGGA

ACTGATGTTG AAAGAGTTAG TAGATCAAAC AGAATAGTAG GAAACAAGAA
TGACTACAAC TTTCTCAATC ATCTAGTTTG TCTTATCATC CTTTGTTCTT

AACATTAAAC TTATACAGGA AAAATGTCTG GCCATATGTT AGTTAGTTCG
TTGTAATTTG AATATGTCCT TTTTACAGAC CGGTATACAA TCAATCAAGC

GGAATGGTTA TTGGTAATTT GTTTTGTATT ATAGCATACA ATAACTAGAG
CCTTACCAAT AACCATTAAA CAAAACATAA TATCGTATGT TATTGATCTC

TTACCAAAGG CTTGTTTTTT CTTGAGCAGT TGAAAGGAGA GACCAATATT
AATGGTTTCC GAACAAAAAA GAACTCGTCA ACTTTCCTCT CTGGTTATAA

TGTGACATGG ATAGTTTCAT GACCACAACT CATTCAATCA TTTTATAGTC
ACACTGTACC TATCAAAGTA CTGGTGTTGA GTAAGTTAGT AAAATATCAG

TATGGCAATA TCCAAGAGAT TGCCAAGAGT AGAAGACAGA ATATTTCATC
ATACCGTTAT AGGTTCTCTA ACGGTTCTCA TCTTCTGTCT TATAAAGTAG

TGACAGTATC TGATTGGTTT ACTGTTTTTC TAATCATATG TGGTCATAAC
ACTGTCATAG ACTAACCAAA TGACAAAAAG ATTAGTATAC ACCAGTATTG

GGGAAGCAGA ATTATGCTTT ATTCAAACAA ACCTGCTTCT GCCTCATTTT
CCCTTCGTCT TAATACGAAA TAAGTTTGTT TGGACGAAGA CGGAGTAAAA

CCTAAGCTAT GAGAACAATT AGAGAAACAG ATTCATGCTT GTATCTTGCA
GGATTCGATA CTCTTGTTAA TCTCTTTGTC TAAGTACGAA CATAGAACGT

TTCAGAAAAC AAACTGTCCT ACTAATCAAA GCTGCAT
AAGTCTTTTG TTTGACAGGA TGATTAGTTT CGACGTA
```

SPINOCEREBELLAR ATAXIA TYPE 8 AND METHODS OF DETECTION

The present application is a continuation application under 37 CFR §1.53(b) of Ser. No. 10/373,667, Confirmation No. 6780, filed on Feb. 24, 2003, entitled SPINOCEREBELLAR ATAXIA TYPE 8 AND METHODS OF DETECTION, which is a continuation application of Ser. No. 09/181,585, filed Oct. 28, 1998, issued as U.S. Pat. No. 6,524,791.

STATEMENT OF GOVERNMENT RIGHTS

The present invention was made with government support under Grant No. P01 NS33718, awarded by the National Institutes of Health. The Government has certain rights in this invention.

BACKGROUND

The ataxias are a clinically and genetically heterogeneous group of neurodegenerative diseases that variably affect the cerebellum, brainstem, and spinocerebellar tracts. Trinucleotide repeat expansions have been shown to be the mutational mechanism responsible for a number of the ataxias as well as other neurological diseases. The underlying molecular mechanism responsible for the pathology associated with these diseases falls into three broad categories. First, the largest group of triplet repeat diseases are those associated with CAG expansions that are translated into polyglutamine tracts. Diseases caused by polyglutamine expansions include spinal and bulbar muscular atrophy, Huntington's disease, and five different forms of dominantly inherited spinocerebellar ataxias (SCAs). A second group involves the 5' CCG expansion that causes fragile X mental retardation and the intronic GAA expansion responsible for Friedreich's ataxia. Both of these result in decreased expression of their corresponding protein products. Finally, a third group involves the expanded CTG repeat in the 3' untranslated region of the dystrophia myotonica-protein kinase coding sequence. This repeat has been shown to cause myotonic dystrophy, but it is not yet understood how this mutation causes an effect at the molecular level.

The ataxias can be dominantly or recessively inherited, or appear with no family history of disease. Among the adult-onset dominant spinocerebellar ataxias (SCAs), seven different loci have been mapped (S. Gispert et al., Nature Genet., 4, 295-299 (1993); Y. Takiyama et al., Nature Genet., 4, 300-304 (1993); K. Gardner et al., Neurology, 44, A361 (1994); S. Nagafuchi et al., Nature Genet., 6, 14-18 (1994); L. P. W. Ranum et al., Nature Genet., 8, 280-284 (1994); A. Benomar et al., Nature Genet., 10, 84-88 (1995); L. G. Gouw et al., Nature Genet., 10, 89-93 (1995); O. Zhuchenko et al., Nature Genet., 15, 62-69 (1997)). Approximately sixty percent of the dominant ataxias result from expansions in trinucleotide CAG repeats at the SCA1, 2, 3, 6 or 7 loci (S. Nagafuchi et al., Nature Genet., 6, 14-18 (1994); O. Zhuchenko et al., Nature Genet., 15, 62-69 (1997); H. T. Orr et al., Nature Genet., 4, 211-226 (1993); Y. Kawaguchi et al., Nature Genet., 8, 221-228 (1994); R. Koide et al., Nature Genet., 6, 9-13 (1994); G. Imbert et al., Nature Genet., 14, 285-291 (1996); S.-M. Pulst et al., Nature Genet., 14, 269-276 (1996); K. Sanpei et al., Nature Genet., 14, 277-284 (1996); G. David et al., Nature Genet., 17, 65-70 (1997); M. D. Koob et al., Nature Genet., 18, 72-75 (1998). The substantial clinical variability among the remaining 40% of the genetically undefined dominant families suggests that a number of additional ataxia coding sequences remain to be identified.

Identifying an ataxia coding sequence can provide an improved method for diagnosis of individuals with the disease and increases the possibility of prenatal/presymptomatic diagnosis or better classification of ataxias.

SUMMARY OF THE INVENTION

To determine whether an individual displaying symptoms of ataxia is suffering from spinocerebellar ataxia the number of CAG repeats in the SCA1, SCA2, SCA3, SCA6, or SCA7 coding sequences present in that individual can be determined. This same type of test can be used for the presymptomatic identification of whether a person may develop the symptoms of spinocerebellar ataxia in the future. In general, a generally high number of CAG repeats in a particular SCA coding sequence indicates that an individual is suffering from spinocerebellar ataxia, or may develop the symptoms of spinocerebellar ataxia in the future. The number of CAG repeats that is indicative of spinocerebellar ataxia typically varies with the type of SCA. Each of these coding sequences of the known types of SCA encodes a polypeptide containing a tract of uninterrupted glutamine amino acids (a polyglutamine tract). However, only approximately 60% of the dominant ataxias are accounted for by the SCA1, SCA2, SCA3, SCA6, and SCA7 coding sequences.

The coding sequence for an eighth spinocerebellar ataxia, spinocerebellar ataxia type 8, has been identified and isolated. The coding sequence is referred to as SCA8. Surprisingly, while the mRNA encoded by the SCA1, SCA2, SCA3, SCA6, and SCA7 coding sequences contains a repeat and is translated into a protein, the mRNA encoded by the SCA8 coding sequence contains repeats with stop codons in all reading frames. As a result, no translated protein has been identified. The isolation of the SCA8 coding sequence allows for the diagnosis of an additional type of spinocerebellar ataxia, spinocerebellar ataxia type 8.

The SCA8 coding sequence contains polymorphic CTA repeats and CTG repeats. The two repeats are located within an approximately 1.2 kb fragment, generally produced by digestion of the candidate region with the restriction enzyme, EcoRI. Generally, the CTA repeat is unstable and can vary between individuals in different families, but typically the number of CTA repeats in the repeat region does not vary between individuals within a family. The CTG repeat is unstable and is typically altered (i.e., expanded or contracted) in individuals with spinocerebellar ataxia type 8 or who are at risk for developing spinocerebellar ataxia type 8. This altered number of CTG repeats can occur both between individuals in different families and between individuals within a family (i.e., from one generation to the next and between siblings). PCR analysis of the region containing the repeats, for instance, demonstrates a correlation between the size of the altered repeat and the risk of displaying at least one symptom of spinocerebellar ataxia type 8. These results demonstrate that SCA8, like hereditary ataxia associated with, for example, SCA1, fragile X syndrome, myotonic dystrophy, X-linked spinobulbar muscular atrophy, and Huntington disease, displays a mutational mechanism involving expansion of at least one unstable trinucleotide repeat.

The present invention provides an isolated nucleic acid molecule containing a repeat region of an isolated spinocerebellar ataxia type 8 (SCA8) coding sequence, the coding sequence located within the long arm of chromosome 13, and a complement of the nucleic acid molecule. Preferably, the nucleic acid is DNA, and which can be genomic DNA or cDNA. In certain embodiments, the SCA8 coding sequence comprises nucleotides 1-448 of SEQ ID NO:1 followed by a repeat region. In other embodiments, the SCA8 coding sequence comprises nucleotides 726-1,159 of SEQ ID NO:1 preceded by a repeat region. Examples of such nucleic acid molecules are set forth in SEQ ID NO:1, SEQ ID NO:2, and SEQ ID NO:3.

In preferred embodiments, the present invention provides an isolated nucleic acid molecule wherein the nucleic acid comprises 1-448 of SEQ ID NO:1, and a complement thereto. Another preferred embodiment includes an isolated nucleic acid molecule comprising nucleotides 1-448 of SEQ ID NO:1 and further comprising a repeat region, and a complement thereto. Yet another preferred embodiment is an isolated nucleic acid molecule wherein the nucleic acid comprises 726-1,159 of SEQ ID NO:1, and a complement thereto. Such molecules can be incorporated into vectors if desired.

The present invention also provides isolated oligonucleotides that can be used as probes and/or primers. In one embodiment, the isolated oligonucleotide includes at least 15 nucleotides from nucleotides 1-448 of SEQ ID NO:1, and the complementary nucleotides thereto. In another embodiment, the isolated oligonucleotide comprising at least 15 nucleotides from nucleotides 726-1,159 of SEQ ID NO:1, and the complementary nucleotides thereto.

In another embodiment, the present invention provides an isolated oligonucleotide that hybridizes to a nucleic acid molecule containing a repeat region of an isolated SCA8 coding sequence; the oligonucleotide having at least about 11 nucleotides. In still another embodiment, the present invention provides an isolated recombinant vector comprising the nucleotides of SEQ ID NO:1 operatively linked to heterologous vector sequences.

The present invention also provides methods. In one embodiment, the present invention provides a method for detecting the presence of a DNA fragment located within an at-risk allele of the SCA8 coding sequence comprising: treating separate complementary DNA molecules of a DNA fragment containing a repeat region of the SCA8 coding sequence with a molar excess of two oligonucleotide primers; extending the primers to form complementary primer extension products which act as templates for synthesizing the desired DNA fragment containing the repeat region; detecting the fragment so amplified; and analyzing the amplified DNA fragment for a repeat region comprising a CTG repeat. Preferably, a first oligonucleotide primer of the two oligonucleotide primers is chosen from nucleotides 1-448 of SEQ ID NO:1, and a second oligonucleotide primer of the two oligonucleotide primers is chosen from nucleotides complementary to nucleotides 726-1,159 of SEQ ID NO:1, wherein each primer has at least 11 nucleotides. More preferably, the first oligonucleotide primer is selected from the group consisting of SEQ ID NO:5, SEQ ID NO:8, and SEQ ID NO:4 and the second oligonucleotide primer is selected from the group consisting of SEQ ID NO:6, SEQ ID NO:9, and SEQ ID NO:12. This method can be carried out using a kit to determine whether or not an individual has, or is at-risk for developing, spinocerebellar ataxia type 8, which is also provided by the present invention. The kit includes the primers described above. Preferably, the step of analyzing comprises analyzing for a repeat region comprising $(CTG)_n$ repeat wherein n is at least about 80. More preferably, the step of analyzing comprises analyzing for a repeat region comprising a combined $((CTG)/(CTA))_n$ repeat (the sum of the CTG and CTA repeats) wherein n is at least about 92.

The present invention provides another method for detecting the presence of at least one DNA molecule containing a repeat region of an SCA8 coding sequence. The method involves: digesting genomic DNA with a restriction endonuclease to obtain DNA fragments; denaturing the DNA fragments to yield DNA molecules and probing the DNA molecules under hybridizing conditions with a detectably labeled probe, which hybridizes to a DNA molecule containing a repeat region of an isolated SCA8 coding sequence; detecting the probe which has hybridized to the DNA molecule; and analyzing the DNA molecule for a repeat region characteristic of a normal or at-risk form of the SCA8 coding sequence. Preferably, the probe is chosen from nucleotides 1-448 of SEQ ID NO:1 or from nucleotides 726-1,159 of SEQ ID NO:1, or complements thereto, wherein the probe has at least 20 nucleotides. In another embodiment, the probe comprises nucleotides 19-449 of SEQ ID NO:1, or a complement thereto. This method can be carried out with a kit for detecting whether or not an individual has, or is at-risk for developing, spinocerebellar ataxia type 8, which is also provided by the present invention. The kit includes a probe chosen from nucleotides 1-448 of SEQ ID NO:1 or from nucleotides 726-1,159 of SEQ ID NO:1, or complements thereto, wherein each probe has at least 20 nucleotides. Preferably, in the method, the step of analyzing comprises analyzing for a repeat region comprising a $(CTG)_n$ repeat wherein n is at least about 80. More preferably, the step of analyzing comprises analyzing for a repeat region comprising a combined $((CTG)/(CTA))_n$ repeat wherein n is at least about 92.

Another method for determining whether an individual has, or is at-risk for developing, spinocerebellar ataxia type 8 involves analyzing a repeat region of a spinocerebellar ataxia type 8 coding sequence wherein individuals who are not at-risk for developing spinocerebellar ataxia type 8 have less than 80 CTG repeats in the repeat region.

Yet another method of the present invention is a method for detecting the presence of a DNA fragment located within an at-risk allele of the SCA8 coding sequence. The method includes: treating separate complementary DNA molecules of a DNA fragment containing a repeat region of the SCA8 coding sequence with a molar excess of a first oligonucleotide primer pair; extending the first primer pair to form complementary primer extension products which act as templates for synthesizing a first desired DNA fragment containing the repeat region; removing the first desired DNA fragment containing the repeat region; treating separate complementary strands of the first desired DNA fragment containing the repeat region with a molar excess of a second oligonucleotide primer pair; extending the second primer pair to form complementary primer extension products which act as templates for synthesizing a second desired DNA fragment containing the repeat region; detecting the second desired DNA fragment so amplified; and analyzing the amplified DNA fragment for a repeat region. Preferably, the first oligonucleotide primer pair comprises a first oligonucleotide primer chosen from nucleotides 1-448 of SEQ ID NO:1, and a second oligonucleotide primer chosen from nucleotides complementary to nucleotides 726-1,159 of SEQ ID NO:1, wherein each primer has at least 11 nucleotides. More preferably, the first oligonucleotide primer is selected from the group consisting of SEQ ID NO:5, SEQ ID NO:8, and SEQ ID NO:4 and the second oligonucleotide primer is selected from the group consisting of SEQ ID NO:6, SEQ ID NO:9, and SEQ ID NO:12. Preferably, the second oligonucleotide primer pair comprises a first oligonucleotide primer chosen from nucleotides 449-725 of SEQ ID NO:1, and a second oligonucleotide primer chosen from nucleotides complementary to nucleotides 726-1,159 of SEQ ID NO:1, wherein each primer has at least 11 nucleotides. More preferably, the second oligonucleotide primer pair comprises a first oligonucleotide primer that has three CTA repeats followed by three CTG repeats and a second oligonucleotide primer chosen from nucleotides complementary to nucleotides 726-1,159 of SEQ ID NO:1. A kit is also provided for carrying out this method that includes these primers.

Definitions

As used herein, "coding sequence" and "coding region" refer to a nucleotide sequence that codes for an mRNA that may or may not be translated into a polypeptide when placed under the control of appropriate regulatory sequences. Preferably, expression of a coding sequence is determined by assaying the level of mRNA expressed by the coding sequence.

As used herein, "repeat region" and "trinucleotide repeat region" refers to the region of an SCA8 coding sequence that typically contains a series of the trinucleotides, preferably a trinucletide CTG (i.e., a CTG repeat) and a series of the trinucleotide CTA (i.e., a CTA repeat). The repeat region of an mRNA encoded by the SCA8 coding sequence typically contains a series of CUA repeats and a series of CUG repeats. The CTG repeat of the repeat region can include nucleotides, and particularly trinucleotides or multiples thereof, other than the trinucleotide CTG.

As used herein, the symptoms of spinocerebellar ataxia type 8 include mild aspiration and gait instability, spastic and ataxic dysarthria, nystagmus, limb and gait ataxia, limb spasticity and diminished vibration perception. Severely affected individuals can become non-ambulatory.

As used herein, an "allele" of SCA8 refers to one of several alternative forms of the nucleotide sequence that occupies the location of the SCA8 coding sequence, which is located on the long arm of chromosome 13. The location of the SCA8 coding sequence on the long arm of chromosome 13 is referred to as the SCA8 locus.

As used herein, "at-risk" describes an individual having an allele of the SCA8 coding sequence that is associated with spinocerebellar ataxia type 8. Herein, this includes an individual who may be manifesting at least one symptom of spinocerebellar ataxia, as well as an individual who may develop at least one symptom of spinocerebellar ataxia in the future. An allele of the SCA8 coding sequence that is associated with spinocerebellar ataxia type 8 is referred to herein as an "at-risk" allele. An individual with an at-risk allele of SCA8 may display at least one symptom of spinocerebellar ataxia type 8 during his or her lifetime. An individual with a "normal" allele of SCA8 will not display symptoms of spinocerebellar ataxia type 8 during his or her lifetime. Whether an individual is considered at-risk generally depends on the number of trinucleotide repeats in the repeat region of the SCA8 coding sequence.

As used herein, "hybridizes," "hybridizing," and "hybridization" means that the oligonucleotide forms a noncovalent interaction with the target DNA molecule under standard conditions. Standard hybridizing conditions are those conditions that allow an oligonucleotide probe or primer to hybridize to a target DNA molecule. Such conditions are readily determined for an oligonucleotide probe or primer and the target DNA molecule using techniques well known to the art, for example see Sambrook et al. *Molecular Cloning: A Laboratory Manual*; Cold Spring Harbor Laboratory: New York (1989). Preferred probes and primers useful in the present invention hybridize to a DNA molecule containing a repeat region of the SCA8 coding sequence under the following conditions: prehybridization at 60° C. for 1 hour in Express Hybe (Clontech, Cat. No. 8015-1) as suggested by the manufacturer, hybridization at 60° C. for 3 hours in Express Hybe with a DNA probe ($4 \times 10^7$ counts, prepared as suggested by manufacturer using Random Primers DNA Labeling System, Gibco BRL, Cat. No. 18187-013), washed 2 times for 15 minutes each at room temperature in 2×SSC, 0.05% SDS, and then washed 2 times for 15 minutes each at 50° C., 0.1% SSC, 0.1% SDS. The nucleotide sequence of a target DNA molecule is generally a sequence complementary to the oligonucleotide primer or probe. The hybridizing oligonucleotide may contain nonhybridizing nucleotides that do not interfere with forming the noncovalent interaction, e.g., a restriction enzyme recognition site to facilitate cloning. The nonhybridizing nucleotides of an oligonucleotide primer or probe may be located at an end of the hybridizing oligonucleotide or within the hybridizing oligonucleotide. Thus, an oligonucleotide probe or primer does not have to be complementary to all the nucleotides of the target DNA sequence as long as there is hybridization under standard hybridization conditions.

As used herein, the term "DNA molecule" refers to a single linear strand of nucleotides.

As used herein, the term "DNA fragment" refers to two DNA molecules that are complementary to each other and hybridized to each other to form a duplex of DNA. As used herein, the term "amplified DNA fragment" refers to a DNA fragment that is a copy of an original DNA fragment. A DNA fragment can be amplified using the polymerase chain reaction (PCR). A DNA fragment can also be amplified by ligating an original DNA fragment to a plasmid and propagating the resulting plasmid in a host cell, e.g., *E. coli*. The amplified DNA fragment is typically identical in nucleotide sequence to at least a portion of the original DNA fragment.

The term "complement" and "complementary" as used herein, refers to the ability of two DNA molecules to base pair with each other, where an adenine on one DNA molecule will base pair to a guanine on a second DNA molecule and a cytosine on one DNA molecule will base pair to a thymine on a second DNA molecule. Two DNA molecules are complementary to each other when a nucleotide sequence in one DNA molecule can base pair with a nucleotide sequence in a second DNA molecule. For instance, the two DNA molecules 5'-ATGC and 5'-GCAT are complementary, and the complement of the DNA molecule 5'-ATGC is 5'-GCAT. The term complement and complementary also encompasses two DNA molecules where one DNA molecule contains at least one nucleotide that will not base pair to at least one nucleotide present on a second DNA molecule. For instance the third nucleotide of each of the two DNA molecules 5'-ATTGC and 5'-GCTAT will not base pair, but these two DNA molecules are complementary as defined herein. Typically two DNA molecules are complementary if they hybridize under the standard conditions referred to above. Typically two DNA molecules are complementary if they have at least about 80% sequence identity, preferably at least about 90% sequence identity.

The term "primer pair," as used herein, means two oligonucleotides designed to flank a region of DNA to be amplified. One primer is complementary to nucleotides present on the sense strand at one end of a DNA fragment to be amplified and another primer is complementary to nucleotides present on the antisense strand at the other end of the DNA fragment to be amplified. The DNA fragment to be amplified can be referred to as the template DNA. The nucleotides of a DNA fragment to which a primer is complementary is referred to as a target sequence or target DNA. A primer can have at least about 11 nucleotides, and preferably, at least about 16 nucleotides and no more than about 35 nucleotides. Typically, a primer has at least about 80% sequence identity, preferably at least about 90% sequence identity with the target DNA to which the primer hybridizes. A primer may serve as a starting point for a DNA polymerase which, in the presence of the necessary materials, synthesizes a DNA molecule that is complementary to the template DNA. Typically, a primer pair is used to amplify a DNA fragment by PCR.

As used herein, the term "isolated" means that a naturally occurring DNA fragment, DNA molecule, coding sequence, or oligonucleotide is removed from its natural environment, or is a synthetic molecule or cloned product. Preferably, the DNA fragment, DNA molecule, coding sequence, or oligonucleotide is purified, i.e., essentially free from any other DNA fragment, DNA molecule, coding sequence, or oligonucleotide and associated cellular products or other impurities.

As used herein, the term "diagnosis" can be the presymptomatic identification of individuals at-risk for ataxia, including the identification of individuals where there is no family history of the disease. Diagnosis can also mean the identification, in an individual displaying at least one symptom of ataxia, of the genetic basis of the at least one symptom.

BRIEF DESCRIPTION OF THE FIGURES

FIG. 7 Nucleotide sequences. a, EcoRI fragment (SEQ ID NO:1) of genomic DNA that includes the repeat region of SCA8. b, mRNA (SEQ ID NO:2) of the SCA8 coding sequence. The mRNA includes the exons D, C, B, and A. c, mRNA (SEQ ID NO:3) of the SCA8 coding sequence. The mRNA includes the exons E, C, and A. d, approximately 700 bp cDNA probe (SEQ ID NO:10) from the 3' untranslated region of the BKRP transcript.

DETAILED DESCRIPTION OF PREFERRED EMBODIMENTS

A. Methods of Diagnosis

Figure 1A:
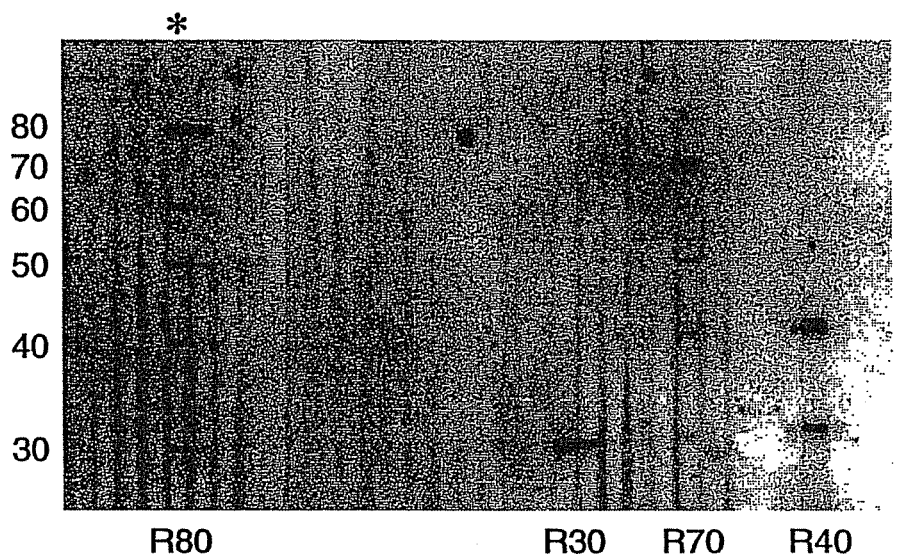
FIG. 1 RAPID cloning of the SCA8 expanded CTG repeat. a, 2D-RED analysis of EcoRI-digested genomic DNA isolated from an individual with a dominantly inherited ataxia (asterisked individual in kindred A, FIG. 2). The size of the RED products generated are indicated at the side of the panel, and the four fractions that generate RED products are indicated below the panel. The genomic DNA size fractions that generate RED30, RED70, and RED40, products contain large nonpathogenic "background" CTG repeats present in many unaffected individuals. The size fraction containing the RED80 CTG expansion (indicated by an asterisk) was unique to this ataxia patient and so was cloned as described. b, RED analysis of CTG-enriched clone pools derived from a RED-positive primary clone pool (see Methods). Each pool contains DNA from 36 individual clones. RED analysis of plasmid DNA from the individual clones in pool 9 identified two clones containing the expanded CTG repeat. Sequence analysis of these clones revealed an expanded CTG tract with 80 uninterrupted repeats.
Figure 1B:
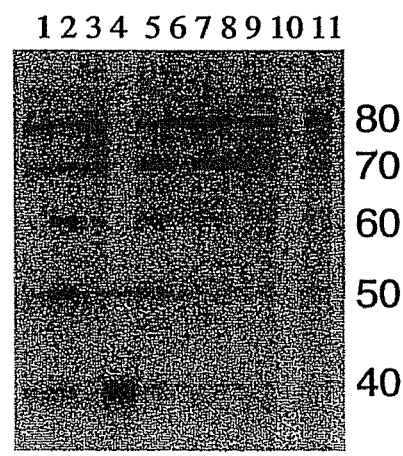

The identification of a coding sequence that is associated with a disease allows for improved diagnosis of the disease. Thus, the present invention relates to methods of diagnosing individuals at-risk of developing spinocerebellar ataxia type 8 as well as those individuals displaying symptoms of the disease. Another aspect of the invention relates to methods of diagnosing individuals not at-risk. In general, the methods can detect the presence of a DNA fragment in genomic DNA or cDNA. Preferably the DNA fragment comprises nucleotides present in genomic DNA. Preferably, the DNA fragment is located within an SCA8 locus of the long arm of chromosome 13. The SCA8 locus can contain an at-risk SCA8 allele or a normal SCA8 allele. The SCA8 locus typically contains a repeat region.

Typically the number of CTG repeats present in the repeat region of an SCA8 allele can be determined. Generally, an at-risk allele of SCM is an allele with at least about 80 CTG repeats in an SCA8 repeat region. Generally, an SCA8 allele with less than 80 CTG repeats is a normal allele, which is indicative of an individual who will not develop symptoms of spinocerebellar ataxia type 8.

Preferably, the number of CTG and CTA repeats present in the repeat region of an SCA8 allele can be determined. An at-risk allele is preferably one with at least about 92 combined CTA and CTG repeats in a repeat region of an SCA8 coding sequence. The number of combined CTA repeats and CTG repeats can be referred to as $((CTG)/(CTA))_n$, where n is the number of CTA repeats and CTG repeats. An SCA8 allele having no greater than about 91 combined CTA and CTG repeats in a repeat region of an SCA8 coding sequence, preferably no greater than about 33, generally indicates an allele of the SCA8 coding sequence that is normal. Generally, for the normal alleles evaluated to date there are some CTA and CTG repeats, typically at least about 16.

The repeat region can have interruptions within the repeats. For example, there can be nonCTG trinucleotide repeats at the 5' side of the CTG repeat, i.e., the side of the CTG repeat that is closest to the CTA repeat. It has been observed that a CTG repeat can include (i) a CCG trinucleotide as the sixth or ninth triplet of a repeat, (ii) a CCG trinucleotide as the sixth through eighth, or sixth through ninth triplets of a repeat, (iii) a CCG trinucleotide as the sixth and fourteenth triplets of a repeat, or (iv) a CCG trinucleotide as the twentieth, twenty seventh, thirty third, and thirty eighth triplets of a repeat. It has also been observed that a CTG repeat can include a CTA trinucleotide as the third and fifth triplets of a repeat. It has also been observed that the CTA and CTG repeats can be separated by up to 6 nucleotides. For instance, SEQ ID NO:1 discloses 6 nucleotides (nucleotides 449-554) between the CTA and the CTG repeats that make up the repeat region. The nucleotides that make up this region between the CTA repeat and CTG repeat varies between different SCA8 alleles, and are absent in some SCA8 alleles, Thus, a CTG repeat having 80 repeats may have a small number of intervening trinucleotides that are not CTG.

The diagnostic methods of the present invention can involve known methods for detecting a specific DNA fragment, including direct detection of the DNA or indirect detection through the detection of RNA, for example. For instance, PCR techniques can be used with novel primers that amplify the repeat region of an SCA8 coding sequence. Alternatively, Southern or Northern blotting hybridization techniques using labeled probes can be used. Other nucleic acid sequencing techniques can also be used for determining the number of trinucleotide repeats. These methods are applicable to individuals who have symptoms of SCA8 or are at risk of developing such symptoms in the future.

In one embodiment of the present invention, DNA probes can be used for identifying DNA fragments or DNA molecules of the at-risk allele of the SCA8 coding sequence. DNA probes are labeled, single-stranded DNA molecules which will hybridize, or noncovalently bind, with a complementary DNA molecule derived from the coding sequence sought to be identified. The probe can be labeled with a suitable label known to those skilled in the art, including radioactive and nonradioactive labels. Typical radioactive labels include $^{32}P$, $^{125}I$, $^{35}S$, and the like. Nonradioactive labels include, for example, ligands such as biotin or digoxigenin as well as enzymes such as phosphatase or peroxidases, or the various chemiluminescers such as luciferin, or fluorescent compounds like fluorescein and its derivatives. The probe may also be labeled at both ends with different types of labels for ease of separation, as, for example, by using an isotopic label at one end and a biotin label at the other end.

The present invention relates to a method for detecting the presence of at least one DNA molecule containing a repeat region where a sample of genomic DNA is fragmented, for instance by digestion with a restriction endonuclease, and the resulting DNA fragments are probed with an oligonucleotide probe. Using DNA probe analysis, the target DNA can be derived by the enzymatic digestion, fractionation, and denaturation of genomic DNA to yield a complex mixture incorporating the DNA from many different coding sequences, including DNA from the long arm of chromosome 13, which includes the SCA8 coding sequence. Preferably, a DNA probe will hybridize only with target DNA. Preferably, the target DNA is the SCA8 coding sequence, a portion of the SCA8 coding sequence, or DNA located near or on the same DNA molecule as the repeat region after digestion with a restriction endonuclease, and the resultant complex can be isolated and identified by techniques known to the art. In one embodiment, the method involves digesting genomic DNA with a restriction endonuclease to obtain DNA fragments, denaturing the fragments to yield DNA molecules, probing the molecules under standard hybridizing conditions with a detectably labeled probe, which hybridizes to a DNA molecule containing a repeat region of an isolated SCA8 coding sequence, detecting probe DNA which has hybridized to the DNA molecules, and analyzing the DNA fragments for a repeat region characteristic of the normal or at-risk forms of the SCA8 coding sequence.

The present invention also provides probes. The probes can be oligonucleotides or longer nucleotide sequences, either synthetic or naturally occurring, capable of hybridizing to the region of the DNA sequence flanking the repeat region and optionally hybridizing to the DNA sequence containing the repeat region. Preferably, the probes hybridize to the SCA8 coding sequence of the long arm of chromosome 13. The probe includes a nucleotide sequence complementary to a portion of a strand of an at-risk or a normal allele of a fragment (preferably an approximately 1.2 kb EcoRI fragment) of an SCA8 coding sequence having a repeat region. The probe sequence can be at least about 20 nucleotides, preferably at least 30 nucleotides. The probes are chosen such that the nucleotide sequence is complementary to a portion of a strand of an at-risk or a normal SCA8 allele, preferably within about 450 nucleotides 5' of the repeat region, including directly adjacent to the repeat region. Preferably, the nucleotide sequence of the probe is chosen from or complementary to nucleotides 1-449 of SEQ ID NO:1. Alternatively, the probes are chosen such that nucleotide sequence is complementary to a portion of a strand of an at-risk or a normal SCA8 allele, preferably within about 435 nucleotides 3' of the repeat region, including directly adjacent to the repeat region. Preferably, the nucleotide sequence of the probe is chosen from or complementary to nucleotides 726-1,159 of SEQ ID NO:1. A nonlimiting example of a probe is nucleotides 19-449 of SEQ ID NO:1 and the nucleotides complementary thereto. This probe will hybridize under the following conditions to an SCA8 allele that has been transferred to nitrocellulose: prehybridization at 60° C. for 1 hour in Express Hybe (Clontech, Cat. No. 8015-1) as suggested by the manufacturer, hybridization at 60° C. for 3 hours in Express Hybe with the DNA probe ($4 \times 10^7$ counts, prepared as suggested by manufacturer using Random Primers DNA Labeling System, Gibco BRL, Cat. No. 18187-013), washed 2 times for 15 minutes each at room temperature in 2×SSC, 0.05% SDS, and then washed 2 times for 15 minutes each at 50° C., 0.1% SSC, 0.1% SDS.

In general, for detecting the presence of a DNA fragment located within the SCA8 coding sequence, the genomic DNA is digested with a restriction endonuclease to obtain DNA fragments. The source of genomic DNA to be tested can be a biological specimen that contains DNA. Examples include specimens of blood, semen, vaginal swabs, tissue, hair, and body fluids. The restriction endonuclease can be one that will cut the genomic DNA into fragments of double-stranded DNA having a particular nucleotide sequence. The specificities of numerous endonucleases are well known and can be found in a variety of publications, e.g. Sambrook et al.; *Molecular Cloning: A Laboratory Manual*; Cold Spring Harbor Laboratory: New York (1989). Preferred restriction endonuclease enzymes include EcoRI, TaqI, and BstNI. EcoRI is particularly preferred.

Diagnosis of the disease can alternatively involve the use of the polymerase chain reaction sequence amplification method (PCR) using novel primers. U.S. Pat. No. 4,683,195

(Mullis et al., issued Jul. 28, 1987) describes a process for amplifying, detecting and/or cloning nucleic acid sequences. This method involves treating separate complementary DNA molecules of a DNA fragment containing a repeat region of the SCA8 coding sequence with a molar excess of two oligonucleotide primers; extending the primers to form complementary primer extension products which act as templates for synthesizing the desired DNA fragment containing the repeat region; detecting the fragment so amplified; and analyzing the amplified DNA fragment for a repeat region.

More specifically, the method steps of treating the DNA fragment with primers and extending the primers include the steps of: adding a pair of oligonucleotide primers, wherein one primer of the pair is complementary to part of the nucleotide sequence in the sense strand of the DNA fragment and the other primer of each pair is complementary to a different part of the same nucleotide sequence in the complementary antisense strand of the DNA fragment; annealing the paired primers to the complementary DNA molecule; simultaneously extending the annealed primers from a 3' terminus of each primer to synthesize an extension product complementary to the strands annealed to each primer wherein the extension products after separation from the complement serve as templates for the synthesis of an extension product for the other primer of each pair; and separating the extension products from said templates to produce single-stranded molecules. Variations of the method are described in U.S. Pat. No. 4,683,194 (Saiki et al., issued Jul. 28, 1987). The polymerase chain reaction sequence amplification method is also described by Saiki et al., *Science,* 230, 1350-1354 (1985) and Scharf et al., *Science,* 324, 163-166 (1986). PCR can be used to detect a nucleotide sequence that contains an SCA8 repeat region.

The present invention also provides primers. The primers are oligonucleotides, either synthetic or naturally occurring, capable of acting as a point of initiating synthesis of a product complementary to the region of the DNA sequence containing the repeat region of the SCA8 coding sequence of the long arm of chromosome 13. Preferably, the primer includes a nucleotide sequence complementary to a portion of a strand of an at-risk or a normal allele of a fragment (preferably an approximately 1.2 kb EcoRI fragment) of an SCA8 coding sequence having a repeat region. The primer sequence can have at least about 11 nucleotides, and preferably, at least about 16 nucleotides and no more than about 35 nucleotides. Typically, the primers are chosen such that they produce a primed product of about 70 base pairs to about 100 base pairs, preferably about 100 base pairs to about 450 base pairs. More preferably, the primers are chosen such that nucleotide sequence is complementary to a portion of a strand of an at-risk or a normal allele within about 150 nucleotides on either side of the repeat region, including directly adjacent to the repeat region.

The first primer of a primer pair can be chosen from the nucleotides 1-448 of SEQ ID NO:1, and the second primer of a primer pair can be chosen from the nucleotides complementary to nucleotides 726-1,159 of SEQ ID NO:1. The primers can be chosen from anywhere within the nucleotides 1-448 of SEQ ID NO:1 and the nucleotides complementary to nucleotides 726-1,159 of SEQ ID NO:1. Preferably, the first primer is SCA8-F3 (5'-TTTGAGAAAGGCTTGTGAGGACT-GAGAATG-3') (SEQ ID NO:5), SCA8-F4 (GTAA-GAGATAAGCAGTATGAGGAAGTATG) (SEQ ID NO:8), or SCA8-F5 (TCAATTCTTTATTCATAAATTCTTAAG) (SEQ ID NO:4). Preferably the second primer is SCA8-R2 (5'-CCTCATGTTAGAAAACTGGCTTT-3') (SEQ ID NO:6), P (GCCCTATCCCAATTCCTTGGCTAGA) (SEQ ID NO:12), or SCA8-R4 (GGTCCTTCATGTTAGAAAAC-CTGGCT) (SEQ ID NO:9). The conditions for amplification of a DNA fragment using the SCA8-F3 and SCA8-R2 primers can be, for instance, 200 µM dNTP, 10 mM Tris pH 9.0, 50 mM KCl, 0.1% Triton X-100, 1.0 mM MgCl$_2$, 10% DMSO, 0.1 U AmpliTaq (Perkin Elmer, Norwalk, Conn.)) cycled 35 times (94° C. for 45 seconds, 53° C. for 75 seconds and 72° C. for 75 seconds).

Alternatively, PCR can be used to amplify the CTG repeat and not the CTA repeat by using a primer pair comprising a first primer derived from the sense strand, i.e., comprising a portion of the nucleotides of SEQ ID NO:1 such that the first primer hybridizes to the nucleotides complementary to SEQ ID NO:1. SEQ ID NO:1 discloses 6 nucleotides (nucleotides 449-554) between the CTA and the CTG repeats that make up the repeat region. The nucleotides that make up the region between the CTA repeats and the CTG repeats varies between different SCA8 alleles, and is absent in some SCA8 alleles. The first primer can comprise at least a portion of the nucleotides that make up the CTA repeat, or the first primer can comprise at least a portion of the nucleotides that make up the CTA repeat and at least a portion of the nucleotides that make up the CTG repeat. For instance, the first primer of the primer pair can comprise no more than 3 CTA repeats followed by less than 9 CTG repeats, preferably no more than 3 CTA repeats followed by no more than 6 CTG repeats, most preferably no more than 3 CTA repeats followed by no more than 3 CTG repeats. A first primer with greater than 3 CTG repeats can be used, provided the length of the CTG repeats does not cause the first primer to bind to CTG repeats present in other locations in the genomic DNA of the individual being tested. To allow for hybridization of a first primer comprising multiples of the CTA and CTG repeats, the hybridization temperature can be decreased. For example, the hybridization temperature can be lowered to at or about 55° C.

Generally, the second primer of the primer pair of this aspect of the invention is complementary to and hybridizes with a part of the nucleotide sequence in the sense strand. Preferably the nucleotide sequence to which the primer hybridizes comprises a short portion (at least about 11 nucleotides, and preferably, at least about 16 nucleotides and no more than about 35 nucleotides) of nucleotides 726-1,159 of SEQ ID NO:1, i.e., nucleotides 3' to the CTG repeat. This aspect of the invention can be practiced with a sample of genomic DNA or cDNA, where the nucleotide sequence to be amplified is a small percentage of the total DNA present.

Alternatively and preferably, this aspect of the invention can be practiced on a fragment of DNA that has already been amplified. For instance, a nucleotide sequence containing a repeat region, i.e., both the CTA and the CTG repeats, can be PCR amplified from a sample of genomic DNA or cDNA using a first primer pair, and the nucleotide sequence amplified by PCR then isolated from the first primer pair and optionally isolated from nonamplified genomic DNA sequences. The isolated amplified nucleotide sequence can be amplified a second time using a second primer pair to amplify the CTG repeat of the repeat region and not the CTA repeat. In this aspect of the invention, preferably the second primer pair hybridizes to nucleotides of the SCA8 coding sequence that are present in the nucleotide sequence amplified by the first primer pair, and the second primer pair amplifies the CTG repeat and not the CTA repeat.

In another alternative embodiment, a DNA fragment containing a repeat region, i.e., both the CTA and the CTG repeats, can be PCR amplified from a sample of genomic DNA or cDNA using a first primer pair, and the amplified DNA fragment then removed from the first primer pair and optionally removed from nonamplified genomic DNA sequences. This amplified DNA fragment can be resolved, for instance on a polyacrylamide gel, to determine the number of CTA and CTG repeats in the DNA fragment. The isolated amplified DNA fragment can be amplified a second time using a second primer pair to amplify the CTA repeat of the repeat region and not the CTG repeat. In this aspect of the invention, preferably the second primer pair hybridizes to nucleotides of the SCA8 coding sequence that are present in the nucleotide sequence amplified by the first primer pair, and the second primer pair amplifies the CTA repeat and not the CTG repeat. This aspect of the invention can be used to determine the number of CTA repeats in a repeat region of an SCA8 allele. Once the number of CTA repeats is determined, it can be used to determine the number of CTG repeats in the DNA fragment.

The regions 5' and 3' to the repeat region of SCA8 are generally 99.9% conserved between different SCA8 alleles. Oligonucleotides suitable for polymerase chain reaction amplification can be selected from the regions flanking the repeat region both 5' and 3' to the repeat region. The regions of the SCA8 coding sequence from which oligonucleotide primers can be selected are from the nucleotides of SEQ ID NO:2 or SEQ ID NO:3, preferably SEQ ID NO:1. Preferred primer pairs are SEQ ID NO:5 and SEQ ID NO:6, SEQ ID NO:4 and SEQ ID NO:12, and SEQ ID NO:8 and SEQ ID NO:9. These primer pairs each successfully amplifies the repeat region of interest using PCR technology. These oligonucleotides are useful for amplifying the repeat region from the SCA8 coding sequence from DNA taken from an individual suspected of having, or at risk for, spinocerebellar ataxia. The amplified fragments can be run on a gel to detect the length of the repeat region and the SCA8 allele classified as at-risk or normal. Alternatively, the primer pair can be used in various known techniques to sequence the SCA8 gene, for instance to determine the numbers of CTG repeats or the number of CTA and CTG repeats.

The invention also relates to a kit for detecting whether or not an individual has, is at-risk for, developing the disease associated with a repeat region. The kit for detecting whether or not an individual has, or is at-risk for, developing the disease associated with a repeat region includes the probes and/or primers disclosed above. Typically, the repeat region detected contains a CTG repeat, preferably a CTG and CTA repeat. Preferably, the repeat region is present in or encoded by the SCA8 coding sequence.

As stated previously, other methods of diagnosis can be used as well. They can be based on the isolation and identification of the repeat region of genomic DNA, cDNA or mRNA. These include, for example, using a variety of electrophoresis techniques to detect slight changes in the nucleotide sequence of the SCA8 coding sequence. Further non-limiting examples include denaturing gradient electrophoresis, single strand conformational polymorphism gels, nondenaturing gel electrophoresis techniques, and DNA chips or microchip arrays of DNA.

The mapping and cloning of the SCA8 coding sequence allows the definitive diagnosis of one type of the dominantly inherited ataxias using a simple test of a biological specimen, for instance blood. This represents the first step towards an unequivocal molecular classification of the dominant ataxias. A simple and reliable classification system for the ataxias is important because the clinical symptoms overlap extensively between the SCA8 and the non-SCA8 forms of the disease. Furthermore, a molecular test for the only known SCA8 mutation permits presymptomatic diagnosis of disease in known SCA8 families and allows for the identification of sporadic or isolated SCA8 repeat region expansions or contractions where there is no family history of the disease. Thus, the present invention can be used in family counseling, planning medical treatment, and in standard work-ups of patients with ataxia of unknown etiology.

B. Cloning Full Length Genes Using Sequences that Flank a Repeat Region

The present invention relates to nucleic acid molecules containing a repeat region, including nucleic acid molecules corresponding to entire coding sequences containing a repeat region and portions thereof. Preferably, the repeat region is the repeat region of an isolated SCA8 coding sequence, and preferably, the nucleic acid molecules corresponding to the entire SCA8 coding sequence and portions thereof. The present invention further relates to vectors and isolated recombinant vectors comprising the entire SCA8 coding sequence and portions thereof, including an isolated recombinant vector comprising the nucleotides of SEQ ID NO:1, SEQ ID NO:2, or SEQ ID NO:3 operatively linked to heterologous vector sequences.

Cloning of DNA into the appropriate replicable vectors provides for determining the sequences that flank a repeat region and subsequent isolation of the full length coding sequence. Cloning allows expression of the mRNA encoded by the coding sequence.

1. Isolation of DNA

DNA containing a coding sequence containing a repeat region may be obtained from a cDNA library prepared from tissue believed to possess the mRNA encoded by the coding sequence and to express it at a detectable level. Alternatively, the SCA8 coding sequence may be obtained from a genomic DNA library or by in vitro oligonucleotide synthesis from the complete nucleotide sequence.

Libraries are screened with appropriate probes designed to identify the coding sequence of interest. Preferably, the probes are derived from the nucleotide sequence on either side of the repeat region. Screening a cDNA or genomic library with the selected probe may be accomplished using standard procedures. Screening cDNA libraries using synthetic oligonucleotides as probes is a preferred method of practicing this invention. The oligonucleotide sequences selected as probes should be of sufficient length and sufficiently unambiguous to minimize false positives. When screening a library that contains DNA from different species, the actual nucleotide sequence(s) of the probe(s) is usually designed based on regions of the nucleotides flanking the extended repeat that have the least codon redundancy. The oligonucleotides may be degenerate at one or more positions, i.e., two or more different nucleotides may be incorporated into an oligonucleotide at a given position, resulting in multiple synthetic oligonucleotides. The use of degenerate oligonucleotides is of particular importance where a library is screened from a species in which preferential codon usage is not known.

The oligonucleotide can be labeled such that it can be detected upon hybridization to DNA in the library being screened. A preferred method of labeling is to use ATP and polynucleotide kinase to radiolabel the 5' end of the oligonucleotide. However, other methods may be used to label the oligonucleotide, including, but not limited to, biotinylation or enzyme labeling.

An alternative means to isolate the coding sequence containing a repeat region is to use PCR methodology. This method requires the use of oligonucleotide primer probes that will hybridize to the SCA8 coding sequence. Strategies for selection of PCR primer oligonucleotides are described below.

2. Insertion of DNA into Vector

The nucleic acid (e.g., cDNA or genomic DNA) containing the coding sequence containing a repeat region is preferably inserted into a replicable vector for further cloning (amplification of the DNA) or for expression of the mRNA encoded by the coding sequence. Many vectors are available, and selection of the appropriate vector will depend on: 1) whether it is to be used for DNA amplification or for expression of the mRNA; 2) the size of the nucleic acid to be inserted into the vector; and 3) the host cell to be transformed with the vector.

Construction of suitable vectors employs standard ligation techniques known in the art. Isolated plasmids or DNA fragments are cleaved, tailored, and religated in the form desired to generate the plasmids required. Typically, the ligation mixtures are used to transform *E. coli* and successful transformants are selected by ampicillin or tetracycline resistance where appropriate. Plasmids from the transformants are prepared, analyzed by restriction endonuclease digestion, and/or sequenced by methods known in the art. See, e.g., Messing et al., *Nucl. Acids Res.*, 9, 309 (1981) and Maxam et al., *Methods in Enzymology*, 65, 499 (1980).

Replicable cloning, and expression vector components generally include, but are not limited to, one or more of the following components: a signal sequence, an origin of replication, one or more marker coding sequences, an enhancer element, a promoter and a transcription termination sequence. At this time a large number of each of these components that are recognized by a variety of potential host cells are well known to the art. It is also well known to the art that a component can be removed from its source DNA using standard molecular biology techniques and used in conjunction with other components that are endogenous to a particular species. Alternatively, heterologous components can be used together to result in the stable replication of a cloned DNA, or the expression of an mRNA encoded by a cloned DNA. A non-limiting description of components that can be used in cloning coding sequences containing trinucleotide repeats can be found in U.S. patent application Ser. No. 08/267,803, filed Jun. 28, 1994.

3. Host Cells

Suitable host cells for cloning or expressing the vectors herein are prokaryotes, filamentous fungi, yeast, protozoa, and higher eukaryotic cells including vertebrate, invertebrate and plant cells. Preferably the host cell should secrete minimal amounts of proteolytic enzymes. Propagation of vectors containing cloned DNA in host cells has become a routine procedure in recent years and is well known to the art.

Alternatively, in vitro methods of cloning, e.g., PCR or other nucleic acid polymerase reactions, are suitable.

4. Transfection and Transformation

Host cells are transfected and preferably transformed with the above-described expression or cloning vectors of this invention and cultured in conventional nutrient media modified as appropriate for inducing promoters, selecting transformants, or amplifying the coding sequences encoding the desired sequences.

Numerous methods of treating a host cell to promote the uptake of a vector containing cloned DNA are known to the art including, for example, calcium phosphate precipitation, electroporation, calcium chloride treatment, nuclear injection, protoplast fusion or microprojectile bombardment may also be used.

The culture of host cells containing the cloning vector in suitable media so as to promote viability of the host cells and carriage of the cloning vector is well known to the art. Any necessary supplements may also be included at appropriate concentrations that would be known to those skilled in the art. The culture conditions, such as temperature, pH, and the like will be apparent to the ordinarily skilled artisan. The host cells referred to in this disclosure encompass in vitro culture as well as cells that are within a host animal.

Objects and advantages of this invention are further illustrated by the following examples, but the particular materials and amounts thereof recited in these examples, as well as other conditions and details, should not be construed to unduly limit this invention.

Experimental Section

All of the dominant forms of spinocerebellar ataxia for which coding sequences have been identified (SCAT, 2, 3, 6, and 7) are caused by the expansion of a CAG repeat that is translated as a polyglutamine tract. To determine if other forms of ataxia share this mutational mechanism, Repeat Expansion Detection (RED) for CAG repeats was performed on DNA samples from a collection of ataxia families (L. P. W. Ranum et al., *Am. J. Hum Genet.*, 57, 603-608 (1995)) with unknown forms of dominantly inherited ataxia. The identification of a previously undescribed CTG expansion responsible for a novel form of spinocerebellar ataxia (SCA8) is described.

a. Methods

RED, 2D-RED, and RAPID Cloning

Figure 2:
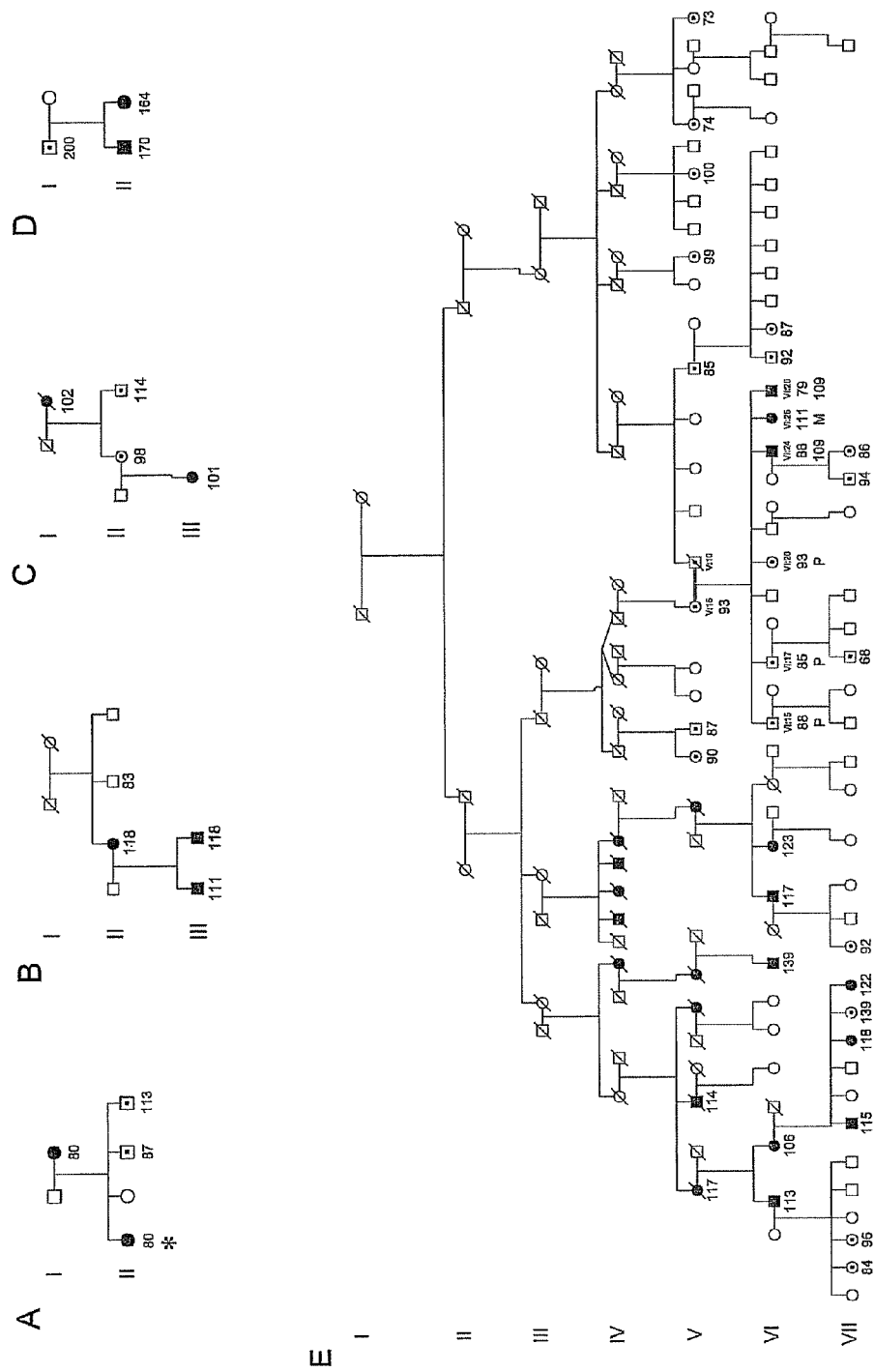
FIG. 2 Five ataxia kindreds positive for the SCA8 CTG repeat expansion are shown. Filled symbols refer to individuals with ataxia, symbols with a dot indicate individuals that have inherited the CTG expansion but are not clinically affected by ataxia. The CTG repeat lengths of expanded alleles are indicated below the symbols. The patient from whom the expanded CTG was isolated is indicated with an asterisk in kindred A. Sequence interruptions of the CTG repeat expansions found within family E allowed us to distinguish the expanded alleles contributed by V:15 and V:16 to their offspring the "M" or "P" indicate that the allele containing the CTG expansion was inherited maternally or paternally, respectively.

Repeat Expansion Detection (RED), two-dimensional RED (2D-RED), and RAPID cloning of the SCA8 allele were performed as described (M. D. Koob et al., *Nature Genet.*, 18, 72-75 (1998)). Briefly, genomic DNA was isolated using standard procedures from the proband of kindred A (FIG. 2). The isolated DNA was digested with EcoRI for use in subsequent 2D-RED and RAPID cloning procedures as described in L. P. W. Ranum et al., U.S. application Ser. No. 09/135,994, filed Aug. 18, 1998. The RED-positive fraction was used to generate a subgenomic library consisting of approximately $5 \times 10^5$ clones. Ten clone pools of approximately $5 \times 10^4$ clones were individually screened for RED$^+$ clones; one of these pools generated a RED80 product. Plasmids from this pool were then enriched for clones containing the CAG expansion using a $(CTG)_{10}$ oligo as described (M. D. Koob et al., supra), and the resulting clones were screened in pools of 36 individual clones. Clones from one of the RED+ pools were then individually screened; two clones that generated RED80 products were identified from this pool. The 1.2 kb insert containing the CTG expansion and flanking genomic DNA was then sequenced (SEQ ID NO:1).

PCR Assay of Expanded SCA8 Repeats

The SCA8 repeat expansion assay was done with SCA8-F3 (5'-TTTGAGAAAGGCTTGTGAGGACTGAGAATG-3') (SEQ ID NO:5) and SCA8-R2 (5'-CCTCATGTTA-GAAAACTGGCTTT-3') (SEQ ID NO:6) primers in a PCR reaction (200 μM dNTP, 10 mM Tris pH 9.0, 50 mM KCl, 0.1% Triton X-100, 1.0 mM $MgCl_2$, 10% DMSO, 0.1 U AmpliTaq (Perkin Elmer, Norwalk, Conn.)) cycled 35 times (94° C. for 45 seconds, 53° C. for 75 seconds and 72° C. for 75 seconds). Southern analysis of EcoRI digested genomic DNA was used to confirm the size of expansion alleles that were too large to be reliably amplified by PCR (i.e., those alleles with >200 repeats). The probe was an approximately 340 bp cDNA SCA8 probe comprising nucleotides 267-604 of SEQ ID NO:3 that included all of exon C and the portion of exon A 5' of the CTG repeat and was labeled with the kit Random Prime (GIBCO BRL, Rockville, Md.) as suggested by the manufacturer. DNA samples from the grandparents of the panel of 40 Centre d'Etude du Polymorphisme Humain (CEPH) reference families (Coriell, Camden, N.J.) and spouses of patients with known forms of ataxia were used as normal controls for the SCA8 PCR assay.

Mapping of the SCA8 Expansion

The SCA8 repeat was physically mapped by screening CEPH Human YAC DNA pools (Research Genetics, Huntsville, Ala., product numbers 95011A and 95011B) with the PCR assay described above. Briefly, PCR analysis was performed on DNA aliquots of pooled YACs using primers SCA8-F3 and SCA8-R2 to identify the YAC clones that contained the SCA8 CTG repeat. Three overlapping YACs (758B1, 744F11, and 810G9) were identified. Subsequent PCR analysis using primers SCA8-F3 and SCA8-R2 confirmed that the overlapping YAC's contained the SCA8 CTG repeat.

These YACs are part of a large YAC contig that has been mapped to chromosome 13q21. Localization to chromosome 13 was independently confirmed using a chromosome cell hybrid panel NIGMS Panel #2 (Coriell, Camden, N.J.). Briefly, PCR analysis was performed on DNA aliquots using primers SCA8-F3 and SCA8-R2 to identify the human chromosome that contained the SCA8 CTG repeat.

Linkage Analysis

Linkage analyses (see, e.g., Ott, J., *Analysis of Human Genetic Linkage*, revised edition, The Johns Hopkins University Press, Baltimore, 1991) were performed using the LINKAGE package of computer programs (version 5.1) as suggested by the developers of the programs (G. M. Lathrop et al., *Proc. Natl. Acad. Sci. USA*, 81, 3443-3446 (1984)). Five age-dependent penetrance classes were established for at-risk unaffected individuals based on the age-at-onset profile for the family (0-20 yr, 10%; 21-30 yr, 30%; 31-45 yr, 50%; 46-60 yr, 60%; over 60 yr, 70%). Affected individuals and unaffected spouses were classified separately. The incidence of ataxia in the general population was estimated to be 1/10,000. Allele frequencies for the SCA8 marker were based on data from CEPH grandparents.

Cloning and Sequencing SCA8 Alleles

PCR was performed using the XL PCR kit from Perkin Elmer (Norwalk, Conn.) using the supplied buffer with 1.0 mM Mg(OAc)$_2$, 10% DMSO, 3 U rTth DNA polymerase, XL, and primers SCA8-F4 (GTAAGAGATAAGCAGTATGAGGAAGTATG) (SEQ ID NO:8) and SCA8-R4 (GGTCCTTCATGTTAGAAAACCTGGCT) (SEQ ID NO:9) cycled as described above in "PCR assay of expanded SCA8 repeats." PCR products were agarose gel-purified, phosphorylated (33 mM Tris-Acetate, pH 7.8, 66 mM potassium acetate, 10 mM magnesium acetate, 500 µM DTT, 625 µM ATP, and 5 U T4 Polynucleotide Kinase (Epicentre, Madison, Wis.), incubated at 37° C. for 30 minutes) and cloned into CIP-treated, SmaI-digested pBluescript SK(−) (Stratagene, La Jolla, Calif.) Plasmids were purified using a standard miniprep procedure, and double-stranded dideoxy sequencing was performed on at least two independent clones per PCR product.

Rapid Amplification of cDNA Ends (RACE)

The 5'RACE System (version 2.0) (Gibco BRL Life Technologies, Rockville, Md., Cat. No. 18374-041) was used for rapid amplification of cDNA 5' ends. For reactions using the 5'RACE System, first strand synthesis was carried out as suggested by the manufacturer using Human Brain Cerebellum mRNA (Clontech, Cat. No. 6543-1) and 2.5 pmoles of a cDNA-specific primer (see below). Purification and TdT tailing of the cDNA were carried out as stated in the 5'RACE System manufacturer's protocol.

First round PCR was done with a nested primer designed from sequence 5' of the cDNA primer and the 5'RACE abridged anchor primer provided with the kit. The reaction was done with the Advantage cDNA Polymerase Kit (Clontech), and was cycled 35 times (94° C. for 50 seconds, 65° C. for 4 minutes).

Second round PCR was performed with a 1:20 dilution of the first round product. The primers used in this reaction were a seconded nested primer and the abridged universal amplification primer (AUAP) provided with the 5'RACE system. GeneAmp XL PCR (Perkin Elmer) components were used with the following PCR profile: a hot start at 94° C., then cycled 5 times (94° C. for 30 seconds, 72° C. for 2 minutes); cycled 5 times (94° C. for 30 seconds, 70° C. for 2 minutes); and finally cycled 32 times (94° C. for 30 seconds, 68° C. for 2 minutes).

In the first 5' RACE reaction, first strand synthesis was carried out as suggested by the manufacturer using Human Brain Cerebellum mRNA (Clontech) and 2.5 pmoles of the cDNA-specific primer F5 (TCAATTCTTTATTCATAAATTCTTAAG) (SEQ ID NO:4). The first PCR used the manufacturer supplied AAP primer and the F4 primer (GTAAGAGATAAGCAGTATGAGGAAGTATG) (SEQ ID NO:8). The second nested PCR used the manufacturer supplied AAUP primer and both the I-long primer (GTCTAGCCAAGGAATTGGGATAGGGCTTC) (SEQ ID NO:13) and the C25 primer (GACTCCGCTGGAAACTCTTCAGCCA) (SEQ ID NO:14). The result was the 5' end of the SCA8 transcript.

In the second 5' RACE reaction, first strand synthesis was carried out as suggested by the manufacturer using Human Brain Cerebellum mRNA (Clontech) and 2.5 pmoles of the cDNA-specific primer F27R (TCCATCTTTCTGAAGGTTTGCTCAGCA) (SEQ ID NO:15). The first PCR used the manufacturer supplied AAP primer and the F23R primer (TTGAATGGCCGGTTGATGACAG) (SEQ ID NO:16). The second nested PCR used the manufacturer supplied AAUP primer and the E22R primer (CTGCTGAGTGCCCTGCCCAGGAG) (SEQ ID NO:17). The result was the 5' end of the BKRP transcript.

Marathon-Ready cDNA (cerebellum cDNA, cat. no. 7401-1) (Clontech, Palo Alto, Calif.) was used for both 5' and 3' cDNA ends. For the Marathon-Ready cDNA reactions, three sets of two rounds of nested PCR were performed as described above using the primers AP1 and AP2 provided with the kit and differing SCA8-specific primers (see below), but both reactions used the following PCR profile: a hot start at 94° C., then cycled 5 times (94° C. for 30 seconds, 72° C. for 2 minutes); cycled 5 times (94° C. for 30 seconds, 70° C. for 2 minutes); and finally cycled 25 times (94° C. for 30 seconds, 68° C. for 2 minutes).

In the first Marathon cDNA reaction the first PCR used the AP1 primer and the F4 primer. The second nested PCR used the AP1 primer and the N primer (GTAGTAGTAGTAGTAAAGCCAGGTT) (SEQ ID NO:18). The result was the first portion of the SCA8 transcript.

In the second Marathon cDNA reaction the first PCR used the AP1 primer and the P primer (GCCCTATCCCAATTCCTTGGCTAGA) (SEQ ID NO:12). The second nested PCR used the AP1 primer and the R4 primer (GGTCCTTCATGTTAGAAAACCTGGCT) (SEQ ID NO:20). The result was the 3' polyA end of the SCA8 transcript.

In the third Marathon cDNA reaction the first PCR used the AP1 primer and the D23 primer (ACCCAGCCAGAGTCGCCTGCTCA) (SEQ ID NO:7). The second nested PCR used the AP1 primer and the D24 primer (CTTCATCGTCCTCCCCGTCCTCTT) (SEQ ID NO:11). The result was the 3' polyA end of the BKRP transcript.

Products were resolved on a 1.2% SeaPlaque GTG (FMC BioProducts Chicago, Ill.) low-melting point agarose gel in 1× TAE buffer (40 mM Tris-acetate, 1 mM EDTA). Bands of resolved PCR product were excised with a sterile razor blade and the agarose was enzymatically removed with AgarACE (0.2U; Promega, Madison, Wis.) as described by supplier. The DNA was concentrated by EtOH precipitation, dried and resuspended in 10 µl of 10 mM Tris, 1 mM EDTA 7.5) buffer. The PCR products were then cloned in the SmaI site of the the plasmid vector pBS SK(–) (Stratagene, La Jolla, Calif.). The nucleotide sequence of the PCR insert was determined using standard techniques. Sequence analysis was performed using internet-based software available through the National Center for Biotechnology Information web page (www.ncbi.nlm.nih.gov).

Northern and PolyA+ RNA DOT Blot Analysis

A Human Brain Multiple Tissue Northern (Clontech) and a RNA Master Blot (Clontech) were used for Northern analysis. Initially, an approximately 700 bp cDNA probe (SEQ ID NO:10) from the 3' untranslated region of the BKRP transcript was labeled using Random Prime (GIBCO BRL, Rockville, Md.) and hybridized to both blots using Express Hybe (Clontech). Manufacturers recommendations were used for hybridization and washes. The blots were then stripped and rehybridized with the 340 bp cDNA SCA8 probe comprising nucleotides 267-604 of SEQ ID NO:3 labeled using Random Prime (GIBCO BRL).

B. Results

RAPID Cloning of an Expanded CTG Repeat from an Ataxia Patient

DNA samples from an affected mother and affected daughter from one of the kindreds (kindred A, FIG. 2) from the collection of ataxia families with unknown forms of dominantly inherited ataxia each generated a RED product with 80 CAG repeats (RED80). 2D-RED analysis of EcoRI-digested genomic DNA from the daughter indicated that the RED80 product was not generated by a known CAG expansion (FIG. 1a). To further characterize this CAG expansion, the approximately 1.2 kb EcoRI fragment containing the expansion was cloned using the RAPID cloning procedure and nucleotide sequence of the genomic insert in the resulting clone was determined.

Figures 6A, 6B:
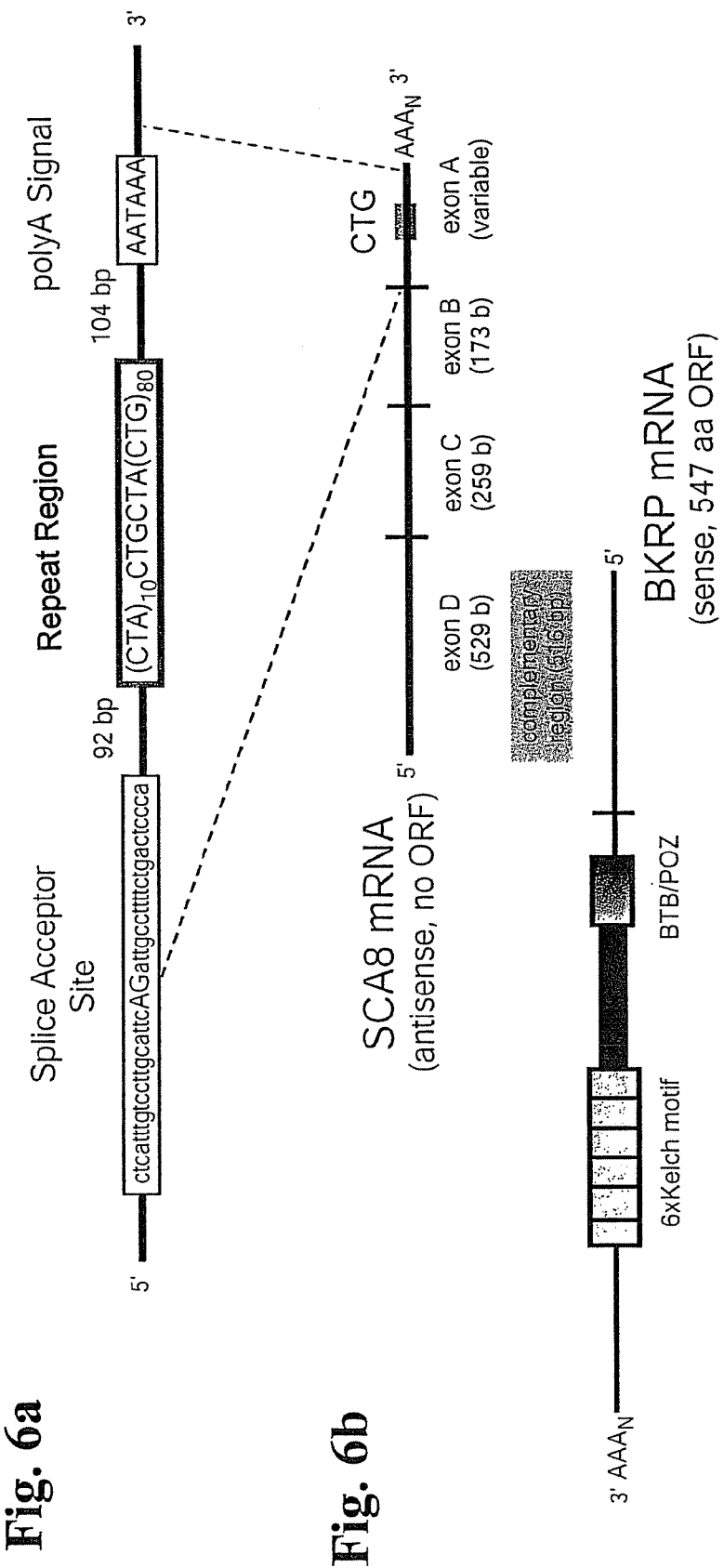
FIG. 6 The genomic (a) and mRNA (b) contexts of the SCA8 repeat region are shown schematically. a, Genomic context of the CTG expansion. The conformation of the CTA and CTG repeats are given ("Repeat Region") for the repeat expansion isolated by RAPID cloning. Only the CTG strand is shown. A splice acceptor site is present in the genomic sequence 5' of the CTG expansion, and a consensus polyadenylation signal is present in the sequence 3' of the repeat. b, The SCA8 repeat is transcribed in the CTG orientation and is present in a fully processed antisense transcript. The horizontal lines represent cDNA sequence, and the vertical lines represent approximate splice junctions. The SCA8 transcript is shown with four exons (A-D), but splice variants were also isolated that only contained exons D, B, and A, or exons E, C, and A (exon E is not shown). Exon D is complementary to a 5' UTR of an mRNA transcribed in the opposite orientation.

Sequence analysis revealed that the expansion consisted of 80 uninterrupted CAG repeats followed by a stretch of 10 TAG repeats (FIG. 6a; the complementary strand containing the CTG and CIA repeats are shown in this figure). There are no significant open reading frames that extend through this expansion, and in particular the reading frame that would produce a polyglutamine expansion contains repeated TAG stop codons. PCR primers were designed from the genomic sequence to amplify across the repeat, and PCR analysis of a chromosome hybrid panel and the CEPH YAC library physically mapped the expansion to chromosome 13q21 near the polymorphic markers D13S275 and D13S135. No ataxia coding sequences have previously been mapped to this locus.

The Expanded CTG Repeat Cosegregates with a Novel Dominant Ataxia (SCA8)

PCR analysis of the CTG repeat was performed on genomic samples from kindred A (FIG. 2). Both of the affected individuals and two at-risk individuals were found to have an expansion in one of their alleles, and the expansion increased in size in two of the three transmissions. The ataxia family collection was screened with this PCR assay and another seven kindreds with ataxia patients that have this expansion were identified. FIG. 2 shows the sizes of the CTG expansions found in individuals from five of these kindreds. The largest of these families (kindred E, FIG. 2) is a seven-generation kindred, of which 89 members were clinically evaluated and tested for expansions. PCR analyses showed that all of the affected individuals in these kindreds had an expanded allele at this locus. Linkage analyses between ataxia and the expansion for kindred E (Table I) gave a maximum LOD score of 6.6. These results indicate that expansions at this locus can cause a novel form of dominantly-inherited spinocerebellar ataxia (SCA8).

The neurologists who evaluated family members from these SCA8 kindreds were blinded to the genetic test results. A total of 25 clinically affected individuals were identified. Age of onset ranged from 10 to 60 years (with a mean±SD of 35±17). The affected family members' age at the time of the initial exam ranged between 37-68 years (mean 48±12) with a disease duration at the time of the exam being 0-35 years. Dysarthria, mild aspiration and gait instability were commonly the initial symptoms. Exam findings included spastic and ataxic dysarthria, nystagmus, limb and gait ataxia, limb spasticity and diminished vibration perception. Severely affected family members were non-ambulatory by the $4^{th}$-$6^{th}$ decades. The patients that are homozygous for the SCA8 expansion and their heterozygous sibling (FIG. 2, kindred E, V1:24-26) were affected to a similar degree, with comparable ages of onset and rates of disease progression.

There were 21 individuals who carried an expanded repeat but were not clinically affected at the time of evaluation. The age at the time of evaluation of the asymptomatic carriers ranged between 14 and 74 years, with a mean (44±17 y) that was comparable to the age of the affected family members. Due to this incomplete penetrance, individuals with the SCA8 form of ataxia did not always have an obvious dominant family history of ataxia. Of the eight SCA8 families identified in our collection, six had been categorized from family history as having a dominant ataxia, one (kindred D) had been categorized as a probable recessive form of ataxia (i.e., multiple affected siblings and unaffected parents), and one (not shown) was an affected individual without a family history of ataxia (sporadic). Excluding the latter two kindreds, SCA8 accounts for 3.4% (6/175) of the dominantly inherited ataxias in our family collection, a frequency similar to SCA1 (10/175) and SCA7 (8/175).

SCA8 Pathogenic Expansions are Large and Unstable

Figure 3A:
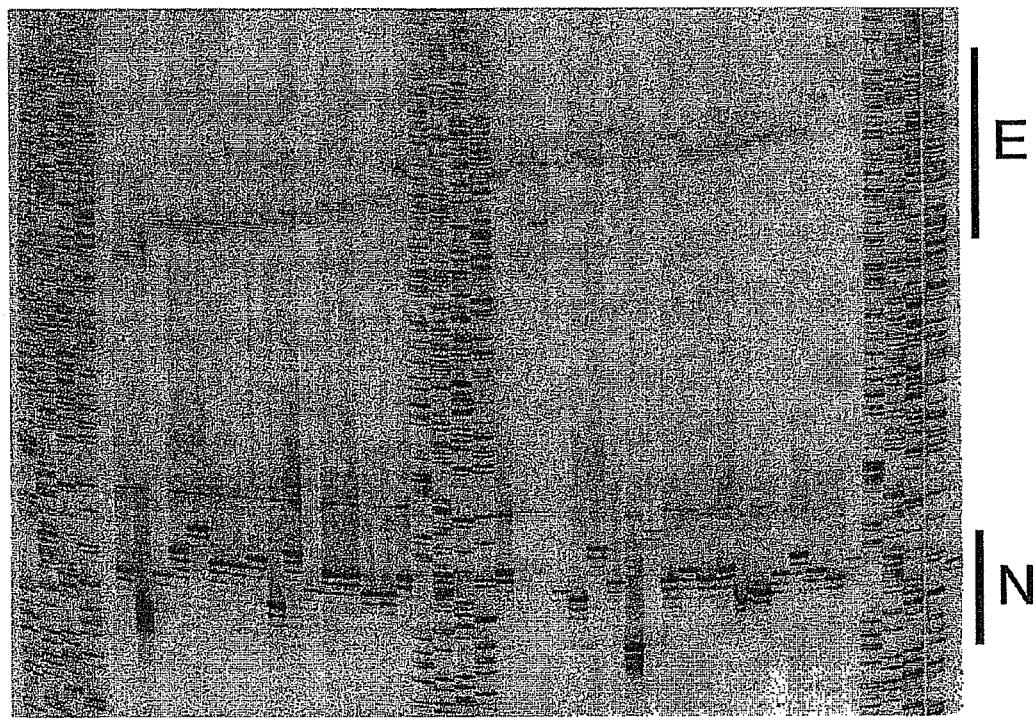
FIG. 3 PCR analysis of SCA8 CTG at-risk and normal alleles. a, PCR sizing of SCA8 alleles in affected and at-risk individuals. The expanded (E) and normal (N) alleles are indicated at the side of the panel. M13 sizing ladders are included for size comparison. b, Distributions of repeat region lengths among control chromosomes (n=692) and SCA8 alleles are shown. A stably transmitted polymorphic CTA (3-17 repeats) is located at the 5' end of the CTG stretch.
Figure 3B:
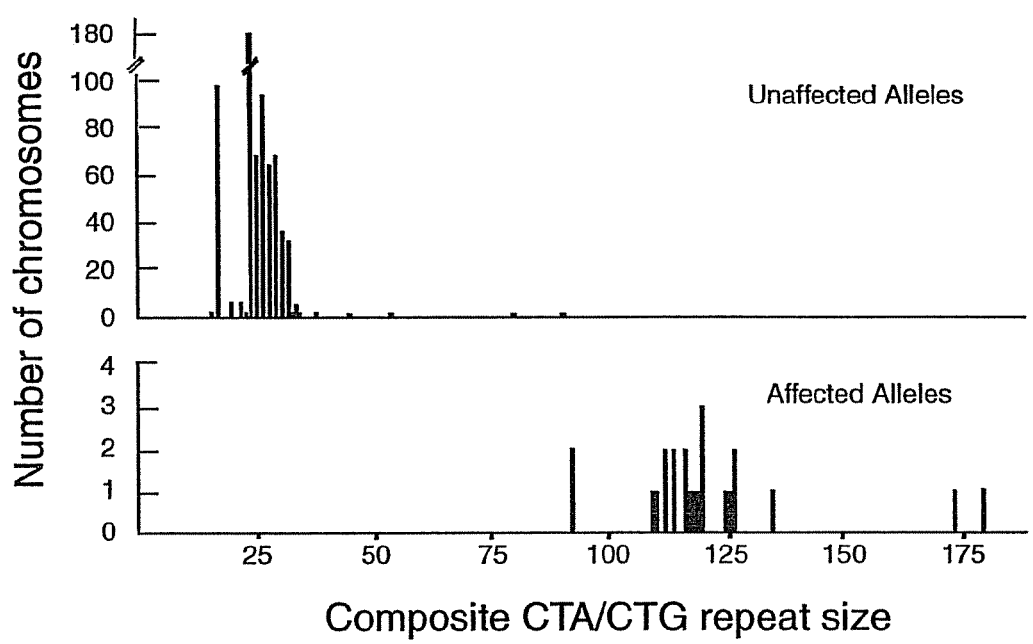

Extensive SCA8 PCR analysis of affected and at-risk individuals has been performed (FIG. 3a) and a panel of control genomic DNA samples representing 692 unaffected alleles has been analyzed. The results of this analysis are summarized in FIG. 3b. Since both the CTG and the CTA repeats are polymorphic, our PCR assay determines the combined size of these two repeats and this is the value that is presented in FIG. 3b. Normal SCA8 alleles with 16 to 91 combined CTG/CTA repeats were found, although >99% of normal alleles had from 19 to 34 total repeats. Among ataxia patients with SCA8 expansions a range of from 92 to 179 combined CTG/CTA repeats was found. Sequencing of affected alleles revealed that the CTA varied in size from 3-17 repeats, but only the CTG repeats were found to be expanded or to change in size from one generation to the next. The size of the CTG expansion alone in affected individuals ranged from 80 to 170 uninterrupted repeats. The size of these affected alleles is considerably larger than what is typically seen for any of the CAG expansions that cause the other SCAs, but is similar in size to the CTG expansions found among adult-onset DM patients (T. Ashizawa et al., *Neurology*, 42, 1877-83 (1992)). One of the largest unaffected alleles (81 combined repeats) was also sequenced and was found to have 68 uninterrupted CTG repeats. The number and location of minor single nucleotide changes to the CTG/CTA repeat motifs found between the uninterrupted CTG and CTA repeat tracts varied widely between many of the sequenced alleles.

Figure 4:
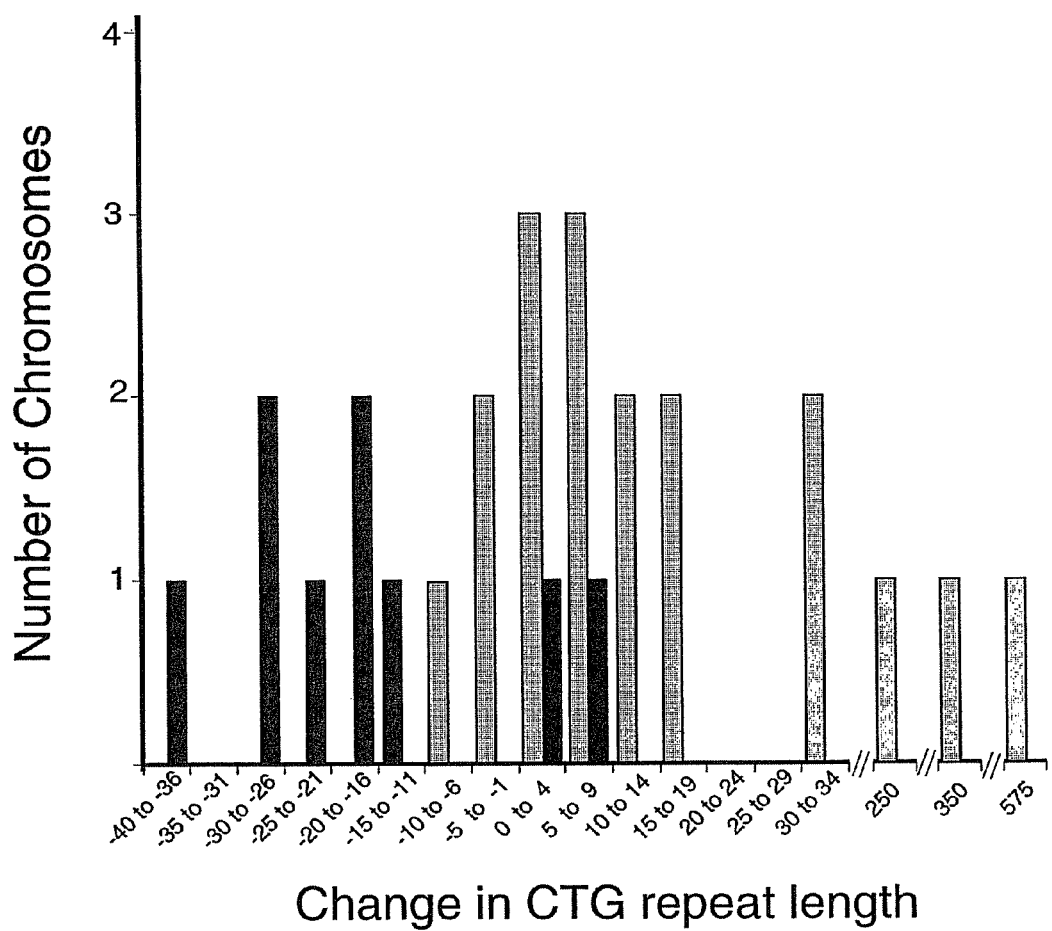
FIG. 4 Intergenerational variation in repeat number for maternal and paternal transmissions. Repeat variation is shown as a decrease (−) or and increase (+) of CTG repeat units. Maternal transmissions are represented by grey bars and paternal transmissions by black bars.

The intergenerational changes in CTG repeat number are typically larger for SCA8 than for the other dominant SCAs, but are generally not as great as for DM. A histogram of the change in CTG repeat number in maternal and paternal transmissions of the SCA8 expansion is shown in FIG. 4. Most paternal transmissions resulted in contractions of the CTG repeat (−36 to +7) (i.e., the expansion changed by the loss of up to 36 repeats to the gain of up to 7 repeats) and most maternal transmissions resulted in expansions (−7 to +575). Three very large increases in repeat length (+250, +350, +575), similar in size to those seen in myotonic dystrophy, all resulted from maternal transmissions. This maternal bias toward expansions has not been reported for the other SCAs (SCA1, SCA2, SCA3, SCA6, and SCA7) but is similar for myotonic dystrophy.

Maternal Bias of Disease Penetrance

Surprisingly, 25 of the 27 documented transmissions of symptomatic SCA8 were maternal (see FIG. 2). Of the 18 asymptomatic individuals with repeat expansions, 3 were maternally transmitted and 15 were transmitted paternally. Kindred D (FIG. 2) is the only kindred with documented paternal transmissions of SCA8. The father, though clinically unaffected, had an unusually large SCA8 expansion (200 repeats) and his clinically affected children inherited smaller but still large CTG expansions (164 and 170 repeats).

Figure 5:
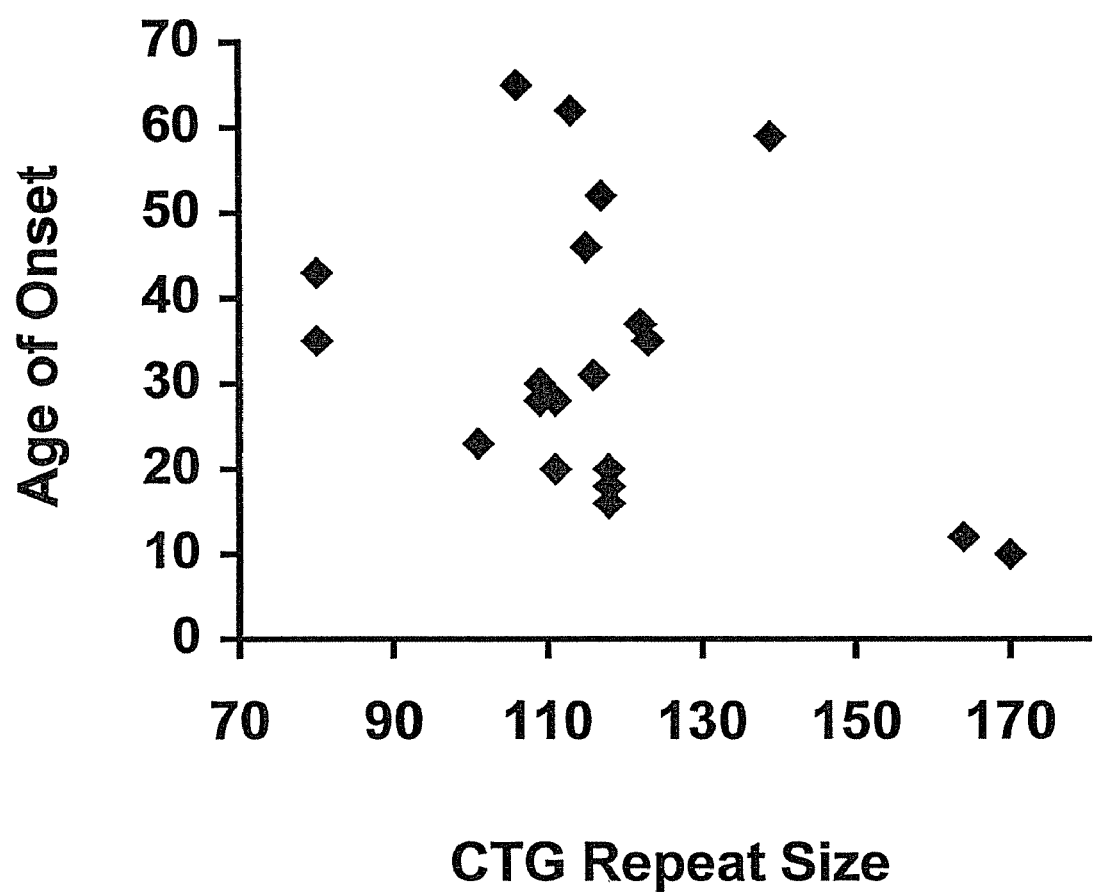
FIG. 5 The relationship between the age of onset and the CTG repeat length of the expanded allele. A correlation coefficient r=−0.33165 was calculated indicating that only 11% ($r^2$=0.11) of the variation in the age of onset can be accounted for by the CTG repeat length on the disease chromosome.

The Size of the SCA8 Expansion is Not Correlated with the Age of Disease Onset or Severity Unlike the other dominant spinocerebellar ataxias, the age of disease onset for SCA8 does not appear to significantly correlated with the size of the CTG expansion (FIG. 5). Four presymptomatic individuals not included in the analysis in FIG. 5 further illustrate that repeat length cannot be used to predict age of onset. The largest SCA8 expansions found (approximately 400, 500, and 700 repeats) are present in at-risk individuals between the ages of 15 and 24 who do not yet show signs of ataxia, and the asymptomatic carrier in kindred D (FIG. 2) has 200 CTG repeats and is still unaffected at age 72. A similar lack of correlation between age of onset and repeat length has also been noted for DM patients with less than approximately 500 CTG repeats.

The severity of the disease course, which varies widely among SCA8 patients, also does not appear to be significantly correlated with a patient's repeat length or with the age of onset. However, that the SCA8 disease course is similar among affected siblings, which may suggest that environmental or genetic factors other than repeat length have a strong influence on the pathology of SCA8.

The SCA8 Trinucleotide Repeat is an Untranslated CTG in a Naturally Occurring Antisense Transcript To identify a cDNA containing the SCA8 CAG repeat a lambda cDNA library constructed from cerebellar mRNA was screened and only a single cDNA clone identified. Sequencing of the insert from this clone revealed that the cDNA was apparently derived from a polyadenylated mRNA transcribed through the SCA8 repeat in the CTG orientation. This result prompted a further analysis of the genomic SCA8 sequence, which revealed the presence of a consensus polyadenylation signal 104 bp 3' of the CTG repeat and a predicted splice acceptor site 112 bp 5' of the CTA repeat (FIG. 6a).

Repeated rounds of RACE were performed to identify the full-length processed SCA8 transcript, which is shown schematically in FIG. 6b. A Marathon RACE procedure (CLONTECH), which identifies either the 3' or 5' ends of linkered cDNAs, and a 5' RACE procedure (BRL), which specifically identifies the 5' ends of mRNA were used. As was expected from the genomic sequence analysis, sequencing of multiple splice-variants confirmed that the CTG repeat is present in the 3' terminal exon that begins at the predicted splice-acceptor site. The longest transcripts identified are 1200 nt in length, excluding the CTG/CTA repeat, and are comprised of four exons. A shorter variant that does not have exon B was also identified. These transcripts have no significant open reading frames and have no significant homology to known coding sequences.

Unexpectedly, a separate set of transcripts up to 3 kb in length were identified when Marathon RACE procedures were performed using primers from the 5' exon D of the SCA8 transcript. Sequencing revealed that these polyadenylated cDNAs contain a long open reading frame but were derived from mRNA transcribed in an orientation opposite to that of the SCA8 transcript. Repeated 5' RACE analysis using primers specific to these transcripts identified a 5' end that lies within exon D of the SCA8 transcript very near the junction of exons D and C (see FIG. 6b). These data indicate that the SCA8 transcript is a naturally occurring antisense RNA that, in its processed form, has a 516 bp overlap with a 3.4 kb mRNA. The 516 base pair overlap corresponds to the first 516 nucleotides of SEQ ID NO:2. The SCA8 CTG repeat is present in the antisense but not the sense transcript.

The open reading frame in the sense mRNA encodes a protein that is 547 amino acids in length and is highly homologous (41% identical, 58% similar amino acids) to the *Drosophila* kelch protein, which is an actin-binding component of ring canals (D. N. Robinson et al., *J. Cell Biol.*, 138, 799-810 (1997)). This new coding sequence was named Brain Kelch-Related Protein (BKRP). BKRP is predicted from sequence analysis to have the POZ/BTB protein:protein interaction domain present in kelch and in a number of zinc finger proteins, and to also have the six "kelch motif" repeats that are thought to constitute the actin-binding domain of kelch. BKRP does not have homology to the amino terminus of kelch responsible for timing the localization of kelch to the ring canal. The domain organization of BKRP is highly similar to that of the recently described kelch-related, nerve-specific human coding sequence NRP/B (T. A. Kim et al., *J. Cell Biol.*, 141, 553-66 (1998)) and the essentially identical mouse coding sequence ENC-1 (M. C. Hernandez et al., *J. Neurosci.*, 17, 3038-51 (1997)) (BKRP is 28% identical and 48% similar to these proteins). The ENC-1 protein, which was identified as a specific molecular marker of neural induction in vertebrates, has been proposed to be involved in the organization of the actin cytoskeleton and NRP/B, which was shown to participate in neuronal process information, is believed to be a nuclear matrix protein.

Multiple-tissue dot blot made with normalized amounts of mRNA from 50 different adult and fetal tissues (RNA Master Blot, Clontech) and a Northern blot made from 8 brain tissues (Human Brain MTN Blot II, Clontech) were sequentially probed with probes specific for BKRP mRNA and the SCA8 antisense transcript. The SCA8 probe detected a very weak signal from most of the tissues represented on the dot blot, but the low level of this signal could not be rigorously differentiated from background hybridization with other transcripts. Despite the fact that SCA8 cDNAs had been generated by PCR-based methods from cerebellar mRNA, the SCA8 probe did not convincingly detect a transcript on the Northern blot. The BKRP probing of the polyA$^+$ dot blot detected the highest level of transcripts in the mRNA from the substantia nigra, lower levels of expression in the cerebellum, frontal lobe, and subthalamic nucleus, and still lower levels in medulla oblongata, kidney and lung. The mRNA from whole fetal brain contained a significantly higher level of BKRP transcript than did mRNA from whole adult brain. A single BKRP transcript approximately 3.5 kb in length was detected on the Northern blot in lanes of mRNA from the cerebellum, medulla, and frontal lobe, but not in lanes with mRNA from cerebral cortex, spinal cord, occipital pole, temporal lobe, and putamen.

Sequence Listing Free Text

SEQ ID NO:2, Description of Artificial Sequence: cDNA comprising exons D, C, B, and A.
SEQ ID NO:3, Description of Artificial Sequence: cDNA comprising exons E, C, and A.
SEQ ID NO:4 through SEQ ID NO: 9 and SEQ ID NO: 11 through SEQ ID NO: 18, Description of Artificial Sequence: Primer.
SEQ ID NO:10, Description of Artificial Sequence: cDNA from BKRP transcript.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method for detecting the presence of a repeat region comprising a CTG repeat within an at-risk allele of an SCA8 coding sequence comprising:

(a) treating separate complementary DNA molecules containing a repeat region of the SCA8 coding sequence with a molar excess of two oligonucleotide primers, which each hybridize to a portion of the SCA8 coding region selected from nucleotides 1-448 and nucleotides 726-1159 of SEQ ID NO:1, nucleotides 1-1070 and nucleotides 1350-1472 of SEQ ID NO:2, and nucleotides 1-636 and nucleotides 915-1037 of SEQ ID NO:3;

(b) extending the primers to foam complementary primer extension products which act as templates for synthesizing a desired DNA fragment containing the repeat region;

(c) detecting the fragment so amplified; and (d) analyzing the amplified DNA fragment for a repeat region comprising a CTG repeat.

2. The method of claim 1 wherein a first oligonucleotide primer of the two oligonucleotide primers is chosen from nucleotides 1-448 of SEQ ID NO:1, and a second oligonucleotide primer of the two oligonucleotide primers is chosen from nucleotides complementary to nucleotides 726-1,159 of SEQ ID NO:1, wherein each primer has at least 11 nucleotides.

3. The method of claim 2 wherein the first oligonucleotide primer is selected from the group consisting of SEQ ID NO:5, SEQ ID NO:8, and SEQ ID NO:4 and wherein the second oligonucleotide primer is selected from the group consisting of SEQ ID NO:6, SEQ ID NO:9, and SEQ ID NO:12.

4. The method of claim 1 wherein the step of analyzing comprises analyzing for a region comprising a combined $(CTG)_n$ repeat wherein n is at least about 80.

5. The method of claim 1 wherein the step of analyzing comprises analyzing for a repeat region comprising a combined $((CTG)/(CTA))_n$ repeat wherein n is at least about 92.

6. A method for detecting the presence of at least one DNA molecule containing a repeat region of an SCA8 coding sequence comprising:
(a) digesting genomic DNA with a restriction endonuclease to obtain DNA fragments;
(b) denaturing the DNA fragments to yield DNA molecules and probing the DNA molecules under hybridizing conditions with a detectably labeled probe, which hybridizes to a repeat region of an isolated SCA8 coding sequence comprising nucleotides 1-448 and nucleotides 726-1159 of SEQ ID NO:1, nucleotides 1-1070 and nucleotides 1350-1472 of SEQ ID NO:2, or nucleotides 1-636 and nucleotides 915-1037 of SEQ ID NO:3;
(c) detecting the probe which has hybridized to the DNA molecule; and
(d) analyzing the DNA molecule for a repeat region characteristic of a normal or at-risk form of the SCA8 coding sequence.

7. The method of claim 6 wherein the probe is chosen from nucleotides 1-448 of SEQ ID NO:1 or from nucleotides 726-1,159 of SEQ ID NO:1, or complements thereto, wherein the probe has at least 20 nucleotides.

8. The method of claim 6 wherein the probe comprises nucleotides 19-449 of SEQ ID NO:1, or a complement thereto.

9. The method of claim 6 wherein the step of analyzing comprises analyzing for a repeat region comprising a $(CTG)_n$ repeat wherein n is at least about 80.

10. The method of claim 6 wherein the step of analyzing comprises analyzing for a repeat region comprising a combined $((CTG/(CTA))_n$ repeat wherein n is at least about 92.

11. A method for detecting the presence of an expanded repeat region located within an at-risk allele of an SCA8 coding sequence comprising:
(a) treating separate complementary DNA molecules containing a repeat region of the SCA8 coding sequence with a molar excess of a first oligonucleotide primer pair, which hybridize to a portion of the SCA8 coding region selected from nucleotides 1-448 and nucleotides 726-1159 of SEQ ID NO:1, nucleotides 1-1070 and nucleotides 1350-1472 of SEQ ID NO:2, and nucleotides 1-636 and nucleotides 915-1037 of SEQ ID NO:3;
(b) extending the first primer pair to form complementary primer extension products which act as templates for synthesizing a first desired DNA fragment containing the repeat region;
(c) removing the first desired DNA fragment containing the repeat region;
(d) treating separate complementary strands of the first desired DNA fragment containing the repeat region with a molar excess of a second oligonucleotide primer pair;
(e) extending the second primer pair to form complementary primer extension products which act as templates for synthesizing a second desired DNA fragment containing the repeat region;
detecting the second desired DNA fragment so amplified; and
(g) analyzing the amplified DNA fragment for an expanded repeat region.

12. The method of claim 11 wherein the first oligonucleotide primer pair comprises a first oligonucleotide primer chosen from nucleotides 1-448 of SEQ ID NO:1, and a second oligonucleotide primer chosen from nucleotides complementary to nucleotides 726-1,159 of SEQ ID NO:1, wherein each primer has at least 11 nucleotides.

13. The method of claim 12 wherein the first oligonucleotide primer is selected from the group consisting of SEQ ID NO:5, SEQ ID NO:8, and SEQ ID NO:4 and wherein the second oligonucleotide primer is selected from the group consisting of SEQ ID NO:6, SEQ ID NO:9, and SEQ ID NO:12.

14. The method of claim 11 wherein the second oligonucleotide primer pair comprises a first oligonucleotide primer chosen from nucleotides 449-725 of SEQ ID NO:1, and a second oligonucleotide primer chosen from nucleotides complementary to nucleotides 726- 1,159 of SEQ ID NO:1, wherein each primer has at least 11 nucleotides.

15. The method of claim 11 wherein the second oligonucleotide primer pair comprises a first oligonucleotide primer that has three CTA repeats followed by three CTG repeats and a second oligonucleotide primer chosen from nucleotides complementary to nucleotides 726-1,159 of SEQ ID NO:1.

16. The method of claim 11 wherein the step of analyzing comprises analyzing for a repeat region comprising a $(CTG)_n$ repeat wherein n is at least about 80.

17. The method of claim 10 wherein the step of analyzing comprises analyzing for a repeat region comprising a combined $((CTG)/(CTA))_n$ repeat wherein n is at least about 92.

* * * * *

UNITED STATES PATENT AND TRADEMARK OFFICE
CERTIFICATE OF CORRECTION

| | | |
|---|---|---|
| PATENT NO. | : 8,247,173 B2 | Page 1 of 1 |
| APPLICATION NO. | : 12/819749 | |
| DATED | : August 21, 2012 | |
| INVENTOR(S) | : Ranum et al. | |

It is certified that error appears in the above-identified patent and that said Letters Patent is hereby corrected as shown below:

Column 32, Line 54
Delete "foam" and insert --form--

Column 34, Line 17
Insert --(f)-- before "detecting the second desired DNA fragment so amplified;"

Signed and Sealed this
Second Day of October, 2012

David J. Kappos
*Director of the United States Patent and Trademark Office*

SEQUENCE LISTING

```
<160> NUMBER OF SEQ ID NOS: 18

<210> SEQ ID NO 1
<211> LENGTH: 1159
<212> TYPE: DNA
<213> ORGANISM: Homo sapiens

<400> SEQUENCE: 1
gaattcatgc ctataattta taagatctgc caccctacca gccttactgt ttttctcatt      60
ggtaatattc atgaagtcac tggtaatttt acattttaaa atatgcagta tgaattgcat     120
atatagtact tcttaaatgt caacacattt atcttaaatc atttatcgaa gtatgagaag     180
tacctatcat attttggtaa ataatacctt taggtttttc ctagttcttg gctccagact     240
aaccatcttg acctgtcatt ctagttttta cttctgagac attctatagt ctgtgtctga     300
tattctctac tatttcctca tttgtccttg cattcagatt gccttttctg actcccagct     360
tccacggaga gattaactct gttggctgaa gccctatccc aattccttgg ctagaccctg     420
ggtccttcat gttagaaaac ctggctttac tactactact actactacta ctactactac     480
tactgctact gctgctgctg ctgctgctgc tgctgctgct gctgctgctg ctgctgctgc     540
tgctgctgct gctgctgctg ctgctgctgc tgctgctgct gctgctgctg ctgctgctgc     600
tgctgctgct gctgctgctg ctgctgctgc tgctgctgct gctgctgctg ctgctgctgc     660
tgctgctgct gctgctgctg ctgctgctgc tgctgctgct gctgctgctg ctgctgctgc     720
tgctgcattt tttaaaaata tattatctta ttttactatt tgatgttata attgttatat     780
atttttccat acttcctcat actgcttatc tcttacttaa gaatttatga ataaagaatt     840 gattttcaa tacatccttc caaaaattat ctgatgttga gttagttgct ctctcttgtg     900
cattctcagt cctcacaagc ctttctcaaa cacaatgttt atcaaagaaa attgtagcaa     960
ccaatatact tagtggaatt tctcacagag tttgagtgta ggaaacagta ttcactgtat    1020
attagtcatt ttgctcccaa tagaaggtgc ataacataaa ttatttaagt ggatgaatgc    1080
tttattttcc tttataaaag taccttcttg cttcactgac atttctatac aactattctt    1140
gtaagcaagg aatgaattc                                                 1159

<210> SEQ ID NO 2
<211> LENGTH: 1471
<212> TYPE: DNA
<213> ORGANISM: artificial
<220> FEATURE:
<223> OTHER INFORMATION: cDNA comprising exons D, C, B, and A
```

<400> SEQUENCE: 2

```
atccttcacc tgttgcctgg ctagagttgt ctggctccac tttgagctct tgcagaacca    60
gccctttttc gtgtggtcca ggaaagtcca tgcctggcac cacctcctcc tctagtgact   120
ccacgtagaa gagagtcctg gctggctgct gagtgccctg cccaggagcc ccttgctgca   180
gcctcgtggc aactggaagc agggtgccat tcagcggatt gaaggaagag gaggaagagg   240
acggggagga cgatgaagag gaagaggagg aaggcttctt ccagaaagtg ctcacaccgc   300
ttctctcttg gcttttgagc aggcgactct ggctgggtcc ccagtgctca aagctgccac   360
tgccgtcctg ttgcaggcag cctcccccg ccggccgcc ggtggaagga cgggtggc       420
tgaagagttt ccagcggagt cgcagaatgt gcttcacatc gaagtctttt cgcccagagc   480
ctgacatgct ttacgcacag aaggcaaaag ctggcagct cacgcagggt tctggaggct   540
gggaagttca agaccaatgc acgagaattt ggtctaaaga gaatcttctt gctctgaaca   600
cacatagtag aaggcagaag ggcaagagag agaacaaagt ctgtgtctcc acatggcaga   660
agagcagagg agacagaacc tactcctcta tggcaaccac cccatcaatg acaaaaatcc   720
tagaaggatg tatgtatagg aagttgaagt gttgagaaga gaatggctca gagtcaagcg   780
ggaacaagat tcaaacttca gagagagagg gaagaaaaac atttaaatat atctggcata   840
atccagacta tttacgacaa gtgttctgtg tttctaataa taaaacagac ttcacctcgg   900
agtacctgca gaactgggac cccaatgacc agggagaatg aagaacaact tgtttgaaga   960
ttgccttttc tgactcccag cttccacgga gagattaact ctgttggctg aagccctatc  1020
ccaattcctt ggctagaccc tgggtccttc atgttagaaa acctggcttt actactacta  1080
ctactactac tactactact actactgcta ctgctgctgc tgctgctgct gctgctgctg  1140
ctgctgctgc tgctgctgct gctgctgctg ctgctgctgc tgctgctgct gctgctgctg  1200
ctgctgctgc tgctgctgct gctgctgctg ctgctgctgc tgctgctgct gctgctgctg  1260
ctgctgctgc tgctgctgct gctgctgctg ctgctgctgc tgctgctgct gctgctgctg  1320
ctgctgctgc tgctgctgct gctgctgcat ttttaaaaa tatattatct tattttacta  1380
tttgatgtta taattgttat atattttttc atacttcctc atactgctta tctcttactt  1440
aagaatttat gaataaagaa ttgattttc a                                  1471
```

<210> SEQ ID NO 3
<211> LENGTH: 1037
<212> TYPE: DNA
<213> ORGANISM: artificial
<220> FEATURE:
<223> OTHER INFORMATION: cDNA comprising exons E, C, and A

<400> SEQUENCE: 3

```
aagcgtaccc ctcgccagat ctcttggtgc acctgcgccc ctgtccctgg ccttttcgag    60
gatgccccga tagcctgccg ggtggctctg agaaagtcaa ttgctttctg caatgccaga   120
agaggtggtt ttatatagtc agtttgtaaa agagaaaaat agatattcta gcgcatatag   180
ggaggcaaaa gaaaaagccc gcctgtgaag ctgtcaaggt cctcacagta caatttctc   240
tctgcctcag cgcctcctcc tccccttct ggaggctggg aagttcaaga ccaatgcacg   300
agaatttggt ctaaagagaa tcttcttgct ctgaacacac atagtagaag gcagaagggc   360
aagagagaga acaaagtctg tgtctccaca tggcagaaga gcagaggaga cagaacctac   420
tcctctatgg caaccacccc atcaatgaca aaaatcctag aaggatgtat gtataggaag   480
ttgaagtgtt gagaagagaa tggctcagag tcaagcggga acaagattgc cttttctgac   540
```

-continued

```
tcccagcttc cacggagaga ttaactctgt tggctgaagc cctatcccaa ttccttggct    600
agaccctggg tccttcatgt tagaaaacct ggctttacta ctactactac tactactact    660
actactacta ctgctactgc tgctgctgct gctgctgctg ctgctgctgc tgctgctgct    720
gctgctgctg ctgctgctgc tgctgctgct gctgctgctg ctgctgctgc tgctgctgct    780
gctgctgctg ctgctgctgc tgctgctgct gctgctgctg ctgctgctgc tgctgctgct    840
gctgctgctg ctgctgctgc tgctgctgct gctgctgctg ctgctgctgc tgctgctgct    900
gctgctgctg ctgcattttt taaaaatata ttatcttatt ttactatttg atgttataat    960
tgttatatat ttttccatac ttcctcatac tgcttatctc ttacttaaga atttatgaat   1020
aaagaattga tttttca                                                  1037
```

<210> SEQ ID NO 4
<211> LENGTH: 27
<212> TYPE: DNA
<213> ORGANISM: artificial
<220> FEATURE:
<223> OTHER INFORMATION: primer

<400> SEQUENCE: 4
tcaattcttt attcataaat tcttaag                                        27

<210> SEQ ID NO 5
<211> LENGTH: 30
<212> TYPE: DNA
<213> ORGANISM: artificial
<220> FEATURE:
<223> OTHER INFORMATION: primer

<400> SEQUENCE: 5
tttgagaaag gcttgtgagg actgagaatg                                     30

<210> SEQ ID NO 6
<211> LENGTH: 23
<212> TYPE: DNA
<213> ORGANISM: artificial
<220> FEATURE:
<223> OTHER INFORMATION: primer

<400> SEQUENCE: 6
cctcatgtta gaaaactggc ttt                                            23

<210> SEQ ID NO 7
<211> LENGTH: 23
<212> TYPE: DNA
<213> ORGANISM: artificial
<220> FEATURE:
<223> OTHER INFORMATION: primer

<400> SEQUENCE: 7
acccagccag agtcgcctgc tca                                            23

<210> SEQ ID NO 8
<211> LENGTH: 29
<212> TYPE: DNA
<213> ORGANISM: artificial
<220> FEATURE:
<223> OTHER INFORMATION: primer

<400> SEQUENCE: 8
gtaagagata agcagtatga ggaagtatg                                      29

```
<210> SEQ ID NO 9
<211> LENGTH: 26
<212> TYPE: DNA
<213> ORGANISM: artificial
<220> FEATURE:
<223> OTHER INFORMATION: primer

<400> SEQUENCE: 9
ggtccttcat gttagaaaac ctggct                                          26

<210> SEQ ID NO 10
<211> LENGTH: 682
<212> TYPE: DNA
<213> ORGANISM: artificial
<220> FEATURE:
<223> OTHER INFORMATION: cDNA from BKRP transcript

<400> SEQUENCE: 10
agtggacaca gatggcttcc ttgaatattg ggagagcagg tgcctgtgtg gtagtcatca     60
agcaaccttg acttattgat attttacttg gaaagatttt acttgctgga gtggttattt    120
ttatattgaa tggcaagaat gagaacttcc agagatgaaa actcttcaag aacaaggatc    180
tctgtagcgt tacctactga tgttgaaaga gttagtagat caaacagaat agtaggaaac    240
aagaaaacat taaacttata caggaaaaat gtctggccat atgttagtta gttcgggaat    300
ggttattggt aatttgtttt gtattatagc atacaataac tagagttacc aaaggcttgt    360
tttttcttga gcagttgaaa ggagagacca atatttgtga catggatagt ttcatgacca    420
caactcattc aatcatttta tagtctatgg caatatccaa gagattgcca agagtagaag    480
acagaatatt tcatctgaca gtatctgatt ggtttactgt ttttctaatc atatgtggtc    540
ataacgggaa gcagaattat gctttattca aacaaacctg cttctgcctc attttcctaa    600
gctatgagaa caattagaga aacagattca tgcttgtatc ttgcattcag aaaacaaact    660
gtcctactaa tcaaagctgc at                                             682

<210> SEQ ID NO 11
<211> LENGTH: 24
<212> TYPE: DNA
<213> ORGANISM: artificial
<220> FEATURE:
<223> OTHER INFORMATION: primer

<400> SEQUENCE: 11
cttcatcgtc ctccccgtcc tctt                                            24

<210> SEQ ID NO 12
<211> LENGTH: 25
<212> TYPE: DNA
<213> ORGANISM: artificial
<220> FEATURE:
<223> OTHER INFORMATION: primer

<400> SEQUENCE: 12
gccctatccc aattccttgg ctaga                                           25

<210> SEQ ID NO 13
<211> LENGTH: 29
<212> TYPE: DNA
<213> ORGANISM: artificial
<220> FEATURE:
<223> OTHER INFORMATION: primer

<400> SEQUENCE: 13
gtctagccaa ggaattggga tagggcttc                                       29
```

```
<210> SEQ ID NO 14
<211> LENGTH: 25
<212> TYPE: DNA
<213> ORGANISM: artificial
<220> FEATURE:
<223> OTHER INFORMATION: primer

<400> SEQUENCE: 14
gactccgctg gaaactcttc agcca                                         25

<210> SEQ ID NO 15
<211> LENGTH: 27
<212> TYPE: DNA
<213> ORGANISM: artificial
<220> FEATURE:
<223> OTHER INFORMATION: primer

<400> SEQUENCE: 15
tccatctttc tgaaggtttg ctcagca                                       27

<210> SEQ ID NO 16
<211> LENGTH: 22
<212> TYPE: DNA
<213> ORGANISM: artificial
<220> FEATURE:
<223> OTHER INFORMATION: primer

<400> SEQUENCE: 16
ttgaatggcc ggttgatgac ag                                            22

<210> SEQ ID NO 17
<211> LENGTH: 23
<212> TYPE: DNA
<213> ORGANISM: artificial
<220> FEATURE:
<223> OTHER INFORMATION: primer

<400> SEQUENCE: 17
ctgctgagtg ccctgcccag gag                                           23

<210> SEQ ID NO 18
<211> LENGTH: 25
<212> TYPE: DNA
<213> ORGANISM: artificial
<220> FEATURE:
<223> OTHER INFORMATION: primer

<400> SEQUENCE: 18
gtagtagtag tagtaaagcc aggtt                                         25
```